(12) United States Patent
Chiocca et al.

(10) Patent No.: US 7,214,515 B2
(45) Date of Patent: May 8, 2007

(54) VIRAL DELIVERY SYSTEM FOR INFECTIOUS TRANSFER OF LARGE GENOMIC DNA INSERTS

(75) Inventors: E. Antonio Chiocca, Wakefield, MA (US); Yoshinaga Saeki, Arlington, MA (US); Richard Wade-Martins, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 396 days.

(21) Appl. No.: 10/035,216

(22) Filed: Jan. 4, 2002

(65) Prior Publication Data

US 2002/0110543 A1    Aug. 15, 2002

Related U.S. Application Data

(60) Provisional application No. 60/330,511, filed on Oct. 23, 2001, provisional application No. 60/294,254, filed on May 31, 2001, provisional application No. 60/287,404, filed on May 1, 2001, provisional application No. 60/259,697, filed on Jan. 5, 2001.

(51) Int. Cl.
*C12N 15/64* (2006.01)
*C12N 15/70* (2006.01)
*C12N 15/79* (2006.01)

(52) U.S. Cl. ............... 435/91.41; 435/91.4; 435/320.1
(58) Field of Classification Search ............... 435/320.1
See application file for complete search history.

(56) References Cited

U.S. PATENT DOCUMENTS

| | | | |
|---|---|---|---|
| 5,275,942 A | 1/1994 | Vos | 435/172.3 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/44 |
| 5,688,773 A | 11/1997 | Chiocca et al. | 514/44 |
| 5,691,177 A | 11/1997 | Guber et al. | 435/172.3 |
| 5,695,967 A | 12/1997 | Van Bokkelen et al. | 435/91.1 |
| 5,741,486 A | 4/1998 | Pathak et al. | 424/93.21 |
| 5,756,283 A | 5/1998 | Wilson et al. | 435/5 |
| 5,763,217 A | 6/1998 | Cynader et al. | 435/69.1 |
| 5,763,242 A | 6/1998 | Zhang et al. | 435/172.3 |
| 5,851,808 A | 12/1998 | Elledge et al. | 435/172.3 |
| 5,869,294 A | 2/1999 | Harrington et al. | 435/91.1 |
| 5,888,732 A | 3/1999 | Hartley et al. | 435/6 |
| 5,998,208 A | 12/1999 | Fraefel et al. | 435/455 |
| 6,143,557 A | 11/2000 | Hartley et al. | 435/320.1 |
| 6,143,566 A | 11/2000 | Heintz et al. | 435/463 |
| 6,171,861 B1 | 1/2001 | Hartley et al. | 435/455 |
| 6,270,969 B1 | 8/2001 | Hartley et al. | 435/6 |
| 6,277,608 B1 | 8/2001 | Hartley et al. | 435/91.4 |
| 6,277,621 B1 | 8/2001 | Horsburgh et al. | 435/235.1 |

FOREIGN PATENT DOCUMENTS

| | | |
|---|---|---|
| WO | WO 93/12233 | 6/1993 |
| WO | WO 95/06486 | 3/1995 |
| WO | WO 97/05263 | 2/1997 |
| WO | WO 99/06582 | 2/1999 |
| WO | WO 00/12693 | 3/2000 |
| WO | WO 00/28016 | 5/2000 |
| WO | WO 00/29000 | 5/2000 |
| WO | WO 00/34497 | 6/2000 |
| WO | WO 00/52027 | 9/2000 |
| WO | WO 01/31039 | 5/2001 |
| WO | WO 01/42509 | 6/2001 |

OTHER PUBLICATIONS

Johnston et al. HSV/AAV hybrid amplicon vectors extend transgene expression in human glioma cells. Hum Gene Ther. Feb. 10, 1997;8(3):359-70.*

Ebersole et al. ("Mammalian Artificial Chromosomes: Prospects for Gene Therapy" in Gene Therapy Technologies, Applications and Regulations (Meager, A., Ed.) © 1999, John Wiley & Sons Ltd, pp. 165-178.*

Kim et al. Modification of bacterial artificial chromosome clones using Cre recombinase: introduction of selectable markers for expression in eukaryotic cells, Genome Res. Apr. 1998;8(4):404-12.*

Saeki et al. Herpes simplex virus type 1 DNA amplified as bacterial artificial chromosome in Escherichia coli: rescue of replication-competent virus progeny and packaging of amplicon vectors. Hum Gene Ther. Dec. 10, 1998;9(18):2787-94.*

Wang et al. A hybrid herpesvirus infectious vector based on Epstein-Barr virus and herpes simplex virus type 1 for gene transfer into human cells in vitro and in vivo. J Virol. Dec. 1996;70(12):8422-30.*

Woodfield et al. Vaccinia topoisomerase and Cre recombinase catalyze direct ligation of activated DNA substrates containing a 3'-para-nitrophenyl phosphate ester. Nucleic Acids Res. Sep. 1, 2000;28(17):3323-31.*

Aboody-Guterman, K.S., et al., "Green fluorescent protein as a reporter for retrovirus and helper virus-free HSV-1 amplicon vector-mediated gene transfer into neural cells in culture and in vivo," Neuroreport 8:3801-3808, Rapid Science Publishers (1997).

(Continued)

*Primary Examiner*—Daniel M. Sullivan
(74) *Attorney, Agent, or Firm*—Sterne, Kessler, Goldstein & Fox P.L.L.C.

(57) ABSTRACT

The present invention relates to HSV-based amplicon vectors carrying a genomic DNA fragment, and methods of constructing and using the same. Included within the present invention is a method of converting any large capacity DNA cloning vector, such as a BAC or PAC, into an HSV amplicon or hybrid HSV amplicon using site-specific, or other types of recombination, so that genomic DNA inserts within the BAC or PAC clone can be delivered by infection to a cell, and efficiently expressed. The present invention also relates to a system for the rapid creation of viral vectors carrying transgenes of interest. This aspect of the invention is accomplished through recombination between: (a) a large-capacity cloning vector carrying a viral genome, and (b) a transfer vector containing the transgene of interest. Finally, an expression-ready genomic DNA library is disclosed.

17 Claims, 17 Drawing Sheets

OTHER PUBLICATIONS

Altshuler, D., et al., "Guilt by association," *Nat. Genet.* 26:135-137, Nature Publishing Co. (Oct. 2000).

Antoch, M.P., et al., "Functional Identification of the Mouse Circadian Clock Gene by Transgenic BAC Rescue," *Cell* 89:655-667, Cell Press (1997).

Banerjee, S., et al., "Therapeutic gene delivery in human B-lymphoblastoid cells by engineered non-transforming infectious Epstein-Barr virus," *Nat. Med.* 1:1303-1308, Nature Publishing Co. (1995).

Bilbao, G., et al., "Adenoviral/retroviral vector chimeras: a novel strategy to achieve high-efficiency stable transduction in vivo," *FASEB J.* 11:624-634, Federation of American Societies for Experimental Biology (1997).

Blackwood, E.M. and Kadonaga, J.T., "Going the Distance: A Current View of Enhancer Action," *Science* 281:60-63, American Association for the Advancement of Science (1998).

Bobo, R.H., et al., "Convection-enhanced delivery of macromolecules in the brain," *Proc. Natl. Acad. Sci.* 91:2076-2080, National Academy of Sciences (1994).

Breakfield, X.O., et al., "4. Herpes Simplex Virus Vectors for Tumor Therapy," in: *The Internet Book of Gene Therapy: Cancer Therapeutics*, Sobol, R.E. and Scanlon, K.J., eds., Appleton and Lange, Stamford, Connecticut, pp. 41-56 (1995).

Brune, W., et al., "Forward with BACs new tools for herpesvirus genomics," *Trends Genet.* 16:254-259, Elsevier Trends Journals (Jun. 2000).

Caskey, C.T. and Kruh, G.D., "The HPRT Locus," *Cell* 16:1-9, Massachusetts Institute of Technology (1979).

Chase, M., et al., "An oncolytic viral mutant that delivers the CYP2B1 transgene and augments cyclophosphamide chemotherapy," *Nat. Biotechnol.* 16:444-448, Nature Publishing Co. (1998).

Compton, S.H., et al., "Stable integration of large (>100kb) PAC constructs in HaCaT keratinocytes using an integrin-targeting peptide delivery system," *Gene Ther.* 7:1600-1605, Macmillan Publishers Ltd. (Sep. 2000).

Cunningham, C. and Davidson, A.J., "A Cosmid-Based System for Constructing Mutants of Herpes Simplex Virus Type 1," *Virology* 197:116-124, Academic Press, Inc. (1993).

Davidson, B.L., et al., "Identification of 17 Independent Mutations Responsible for Human Hypoxanthine-Guanine Phosphoribosyltransferase (HPRT) Deficiency," *Am. J. Hum. Genet.* 48:951-958, University of Chicago Press (1991).

Davidson, B.L., et al., "A model system for in vivo gene transfer into the central nervous system using an adenoviral vector," *Nat. Genet.* 3:219-223, Nature Publishing Co. (1993).

Delecluse, H.-J., et al., "Propagation and recovery of intact, infectious Epstein-Barr virus from prokaryotic to human cells," *Proc. Natl. Acad. Sci. USA* 95:8245-8250, National Academy of Sciences (1998).

Dornburg, R., "Reticuloendotheliosis viruses and derived vectors," *Gene. Ther.* 2:301-310, Stockton Press (1995).

During, M.J., et al., "Long-Term Behavioral Recovery in Parkinsonian Rats by an HSV Vector Expressing Tyrosine Hydroxylase," *Science* 266:1399-1403, American Association for the Advancement of Science (1994).

Evans, G.A., et al., "High efficiency vectors for cosmid microcloning and genomic analysis," *Gene* 79:9-20, Elsevier Science B.V. (1989).

Feng, M., et al., "Stable in vivo gene transduction via a novel adenoviral/retroviral chimeric vector," *Nat. Biotechnol.* 15:866-870, Nature Publishing Co. (1997).

Flotte, T.R. and Carter, B.J., "Adeno-associated virus vectors for gene therapy," *Gene Ther.* 2:357-362, Stockton Press (1995).

Fraefel, C., et al., "Helper Virus-Free Transfer of Herpes Simplex Virus Type 1 Plasmid Vectors into Neural Cells," *J. Virol.* 70:7190-7197, American Society for Microbiology (1996).

Fraefel, C., et al., "Gene Transfer into Hepatocytes Mediated by Helper Virus-Free HSV/AAV Hybrid Vectors," *Mol. Med.* 3:813-825, Springer (1997).

Fraefel, C., et al., "4. HSV-1 Amplicon," in: *Gene Therapy for Neurological Disorders and Brain Tumors*, Chiocca, E.A. and Breakefield, X.O., eds., Humana Press, Totowa, New Jersey, pp. 63-82 (1998).

Gardella, T., et al., "Detection of Circular and Linear Herpesvirus DNA Molecules in Mammalian Cells by Gel Electrophoresis," *J. Virol.* 50:248-254, American Society for Microbiology (1984).

Geller, A.I. and Breakefield, X.O., "A Defective HSV-1 Vector Expresses *Escherichia coli* β-Galactosidase in Cultured Peripheral Neurons," *Science* 241:1667-1669, American Association for the Advancement of Science (1988).

Geller, A.I., et al., "An efficient deletion mutant packaging system for defective herpes simplex virus vectors: Potential applications to human gene therapy and neuronal physiology," *Proc. Natl. Acad. Sci. USA* 87:8950-8954, National Academy of Sciences (1990).

Glorioso, J.C., et al., "Chapter 1. Herpes Simplex Virus as a Gene-Delivery Vector for the Central Nervous System," in: *Viral Vectors: Gene Therapy and Neuroscience Applications*, Kaplitt, M.G. and Loewy, A.D., eds. Academic Press, Inc., New York, New York, pp. 1-23, (1995).

Hammerschmidt, W. and Sugden, B., "Identification and Characterization of oriLyt, a Lytic Origin of DNA Replication of Epstein-Barr Virus,"*Cell* 55:427-433, Cell Press (1988).

Hammerschmidt, W. and Sugden, B., "Genetic analysis of immortalizing functions of Epstein-Barr virus in human B lymphocytes" *Nature* 340:393-397, Macmillan Journals Ltd. (1989).

Harrington, J.J., et al., "Formation of de novo centromeres and construction of first-generation human artificial microchromosomes," *Nat. Genet.* 15:345-355, Nature Publishing Co. (1997).

Heise, C., et al., "ONYX-015, an E1B gene-attenuated adenovirus, causes tumor-specific cytolysis and antitumoral efficacy that can be augmented by standard chemotherapeutic agents," *Nat. Med.* 3:639-645, Nature Publishing Co. (1997).

Hooper, M., et al., "HPRT-deficient (Lesch-Nyhan) mouse embryos derived from germline colonization by cultured cells," *Nature* 326:292-295, Macmillan Journals Ltd. (1987).

Horikawa, Y., et al., "Genetic variation in the gene encoding calpain-10 is associated with type 2 diabetes mellitus," *Nat. Genet.* 26:163-175 Nature Publishing Co. (Oct. 2000).

Horsburgh, B.C., et al., "Allele replacement: an application that permits rapid manipulation of herpes simplex virus type 1 genomes," *Gene Ther.* 6:922-930, Stockton Press (1999).

Huschtscha, L.I. and Holliday, R., "Limited and Unlimited Growth of SV40- Transformed Cells from Human Diploid MRC-5 Fibroblasts," *J. Cell. Sci.* 63:77-99, The Company of Biologist Limited (1983).

Ioannou, P.A., et al., "A new bacteriophage P1-derived vector for the propagation of large human DNA fragments," *Nat. Genet.* 6;84-89 Nature Publishing Co. (1994).

Jacoby, D.R., et al., "Hybrid vectors: a new generation of virus-based vectors designed to control the cellular fate of delivered genes," *Gene Ther.* 4:1281-1283, Stockton Press (1997).

Johnston, K.M., et al., "HSV/AAV Hybrid Amplicon Vectors Extend Transgene Expression in Human Glioma Cells," *Hum. Gene Ther.* 8:359-370, Mary Ann Liebert, Inc. (1997).

Kaplitt, M.G., et al., "Long-term gene expression and phenotypic correction using adeno-associated virus vectors in the mammalian brain," *Nat. Genet.* 8:148-154, Nature Publishing Co. (1994).

Kilby, N.J., et al., "Site-specific recombinases: tools for genome engineering," *Trends Genet.* 9:413-421, Elsevier Science Publishers Ltd. (1993).

Kim, U.-J., et al., "Construction and Characterization of a Human Bacterial Artificial Chromosome Library," *Genomics* 34:213-218, Academic Press, Inc. (1996).

Kim, S.Y., et al., "Modification of Bacterial Artificial Chromosome Clones Using Cre Recombinase: Introduction of Selectable Markers for Expression in Eukaryotic Cells," *Genome Res.* 8:404-412, Cold Spring Harbor Laboratory Press (1998).

Kramm, C.M., et al., "Gene Therapy for Brain Tumors," *Brain Pathol.* 5:345-381, International Society of Neuropathology (1995).

Latchman, D.S., et al., "Herpes Simplex Virus Vectors for Gene Therapy," *Mol. Biotechnol.* 2:179-195, Humana Press (1994).

La Gal La Salle, G., et al., "An Adenovirus Vector for Gene Transfer into Neurons and Glia in the Brain," *Science* 259:988-990, American Association for the Advancement of Science (1993).

Li, Q., et al., "Locus control regions coming of age at a decade plus," *Trends Genet.* 15:403-408, Elsevier Science Ltd. (1999).

Lim, F., et al., "Generation of High-Titer Defective HSV-1 Vectors Using and IE 2 Deletion Mutant and Quantitative Study of Expression in Cultured Cortical Cells," *BioTechniques* 20:460-469, Eaton Publishing Co. (1996).

Logvinoff, C. and Epstein, A.L., "Genetic Engineering of Herpes Simplex Virus and Vector and Vector Genomes Carrying loxP Sites in Cells Expressing Cre Recombinase," *Virology* 267:102-110, Academic Press, Inc. (Feb. 2000).

Luckow, V.A., et al., "Efficient Generation of Infectious Recombinant Baculoviruses by Site-Specific Transposon-Mediated Insertion of Foreign Genes into a Baculovirus Geome Propagated in *Escherichia coli*," *J. Virol.* 67:4566-4579, American Society fro Microbiology (1993).

Mejfa, J.E. and Monaco, A.P., "Retrofitting Vectors for *Escherichia coli*-Based Artificial Chromosomes (PACs and BACs) with Markers for Transfection Studies," *Genome Res.* 7:179-186, Cold Spring Harbor Laboratory Press (1997).

Messerle, M., et al., "Cloning and mutagenesis of a herpesvirus genome as an infectious bacterial artificial chromosome," *Proc. Natl. Acad. Sci. USA* 94:14759-14763, National Academy of Sciences (1997).

Monaco, A.P. and Larin, Z., "YACs, BACs, PACs and MACs: artificial chromosomes as research tools," *Trends Biotech.* 12:280-286, Elsevier Science Ltd. (1994).

Morrison, P.F., et al., "High-flow microinfusion: tissue penetration and pharmacodynamics," *Am. J. Physiol.* 266:R292-R305, American Physiological Society (1994).

Nakanishi, M., "Gene Introduction Into Animal Tissues," *Crit. Rev. Ther. Drug Carr. Sys.* 12:263-310, Begell House, Inc. (1995).

Nefedov, M., et al., "Insertion of disease-causing mutations in BACs by homologous recombination in Escherichia coli," *Nucl. Acids Res.* 28:e79i-e79iv, Oxford University Press (Sep. 2000).

Osoegawa, K., et al., "Bacterial Articicial Chromosome Libraries for Mouse Sequencing and Functional Analysis," *Genome Res.* 10:116-128, Cold Spring Laboratiory Press (Jan. 2000).

Pellegrino, L.J. and Cushman, A.J., "Chapter 3. Use of the Stereotaxic Technique," in: *Methods in Psychobiology*, Myers, R.D., ed., Academic Press, New York, New York, pp. 67-90 (1990).

Peterson, K.R., et al., "Use of yeast artificial chromosomes (YACs) for studying control of gene expression: Correct regulation of the genes of a human β-globin locus YAC following transfer to mouse erythroleukemia cell lines," *Proc. Natl. Acad. Sci. USA* 90:11207-11211, National Academy of Sciences (1993).

Preston, C.M., "Control of herpes Simplex Virus Type 1 mRNA Synthesis in Cells Infected with Wild-Type Virus or the Temperature-Sensitive Mutant tsK," *J. Virol.* 29:275-284, American Society for Microbiology (1979).

Robbins, P.D., et al., "Viral vectors for gene therapy," *Trends Biotechnol.* 16:35-40, Elsevier Trends Journals (1998).

Roder, J. and Hickey, W. F., "Mouse models, immunology, multiple sclerosis and myelination," *Nat. Genet.* 12:6-8, Nature Publishing Co. (1996).

Rossant, J. and Nagy, A., "Genome engineering: the new mouse genetics," *Nat. Med.* 1:592-594, Nature Publishing Co. (1995).

Saeki, Y., et al., "Herpes Simplex Virus Type 1 DNA Amplified as Bacterial Artificial Chromosome in Escherichia coli: Rescue of Replication-Competent Virus Progeny and Packaging of Amplicon Vectors," *Hum. Gen. Ther.* 9:2787-2794, Mary Ann Liebert, Inc. (1998).

Saeki, Y., et al., "Improved Helper Virus-Free Packaging System for HSV Amplicon Vectors Using an ICP27 Deleted, Oversized HSV-1 DNA in a Bacterial Artificial Chromosome," *Mol. Ther.* 3:591-601, Academic Press, Inc. (Apr. 2001).

Sauer, B., "Site-specific recombination: developments and applications," *Curr. Opin. Biotechnol.* 5:521-527, Current Biology Ltd. (1994).

Schiedner, G., et al., "Genomic DNA transfer with a high-capacity adenovirus vector results in improved in vivo gene expression and decreased toxicity," *Nat. Genet.* 18:180-183 Nature Publishing Co. (1998).

Sena-Esteves, M., et al., "HSV-1 Amplicon Vectors- Simplicity and Versatility," *Mol. Ther.* 2:9-15, Academic Press, Inc. (Jul. 2000).

Shaughnessy, E., et al., "Parvoviral Vectors for the Gene Therapy of Cancer," *Semin. Oncol.* 23:159-171, W.B. Saunders Co. (1996).

Shizuya, H., et al., "Cloning and stable maintenance of 300-kilobase-pair fragments of human DNA in *Escherichia coli* using an F-factor-based vector," *Proc. Natl. Acad. Sci. USA* 89:8794-8797, National Academy of sciences (1992).

Simon, M.I., "Dysfunctional genomics: BACs to the rescue," *Nat. Biotechnol.* 15:839, Nature Publishing Co. (1997).

Smith, I.L., et al., "Evidence that The Herpes Simplex Virus Immediate Early Protein ICP27 Acts Post-Transcriptionally during Infection to Regulate Gene Expression," *Virology* 186:74-86, Academic Press, Inc. (1992).

Smith, G.A. and Enquist, L.W.,"A self-recombining bacterial artificial chromosome and its application for analysis of herpesvirus pathogenesis," *Proc. Natl. Acad. Sci. USA* 97:4873-4878, National Academy of sciences (Apr. 2000).

Spaete, R.R. and Frenkel, N., "The Herpes Simplex Virus Amplicon: A New Eucaryotic Defective-Virus Cloning-Amplifying Vector," *Cell* 30:295-304, Massachusetts Institute of Technology (1982).

Spaete, R.R. and Frenkel, N., "The herpes simplex virus amplicon: Analyses of cis-acting replication functions," *Proc. Natl. Acad. Sci. USA* 82:694-698, National Academy of Sciences (1985).

Sternberg, N., "Bacteriophage P1 cloning system for the isolation, amplification, and recovery of DNA fragments as large as 100 kilobase pairs," *Proc. Natl. Acad. Sci. USA* 87:103-107, National Academy of Sciences (1990).

Sun, T.-Q., et al., "Human artificial episomal chromosomes for cloning large DNA fragments in human cells," *Nat. Genet.* 8:33-41, Nature Publishing Co. (1994).

Sun, T.-Q., et al., "Engineering a mini-herpesvirus as a general strategy to transduce up to 180 kb of functional self-replicating human mini-chromosomes," *Gene Ther.* 3:1081-1088, Stockton Press (1996).

Vos, J.-M.H., "The simplicity of complex MACs," *Nat. Biotechnol.* 15:1257-1259, Nature Publishing Co. (1997).

Vos, J.-M.H., "Mammalian artificial chromosomes as tools for gene therapy," *Curr. Opin. Genet. Dev.* 8:351-359, Current Biology Ltd. (1998).

Wade-Martins, R., et al., "Long-term stability of large insert genomic DNA episomal shuttle vectors in human cells," *Nucl. Acids Res.* 27:1674-1682, Oxford University Press (1999).

Wade-Martins, R., et al., "Stable correction of a genetic deficiency in human cells by an episome carrying a 115 kb genomic transgene," *Nat. Biotechnol.* 18:1311-1314, Nature Publishing Co. (Dec. 2000).

Wade-Martins, R., et al., "An Infectious transfer and expression system for genomic DNA loci in human and mouse cells," *Nat. Biotechnol.* 19:1067-1070, Nature Publishing Co. (Nov. 2001).

Wang, M., et al., "Human Artificial Episomal Chromosomes (HAECS) for Building Large Genomic Libraries," in: *Human Genome Program, U.S. Department of Energy, Human Genome Program Report, Part 2, 1996 Research Abstracts*, Human Genome Management Information System, Oak Ridge National Laboratory, Oak Ridge, Tennessee, p. 30 (1997).

Wang, S. and Vos, J.-M., "A Hybrid Herpesvirus Infectious Vector Based on Epstein-Barr Virus and Herpes Simplex Virus Type 1 for Gene Transfer into Human Cells In Vitro and In Vivo," *J. Virol.* 70:8422-8430, American Society for Microbiology (1996).

Wang, S., et al., "A novel herpesvirus amplicon system for in vivo gene delivery," *Gene Ther.* 4:1132-1141, Stockton Press (1997).

Wang, X., et al., "Fifty-One Kilobase HSV-1 Plasmid Vector Can Be Packaged Using a Helper Virus-Free System and Supports Expression in the Rat Brain," *BioTechniques* 28:102-107, Eaton Publishing Co. (Jan. 2000).

Watson, J.D., et al., "Working toward Human Gene Therapy," in: *Recombinant DNA, 2nd Ed. Chapter 28*, Watson, J.D., et al., eds. Scientific American Books, New York, New York, pp. 567-581 (1992).

Westphal, E.M., et al., "A System for Shuttling 200-kb BAC/PAC Clones into Human Cells: Stable Extrachromosomal Persistence and Long-Term Ectopic Gene Activation," *Hum. Gene Ther.* 9:1863-1873, Mary Ann Liebert, Inc. (1998).

Wilson, J.M., "Vectors- shuttle vehicles for gene therapy," *Clin. Exp. Immunol. 107* (Suppl. 1):31-32, Blackwell Science Ltd. (1997).

Wohlgemuth, J.G., et al., "Long-term gene expression from autonomously replicating vectors in mammalian cells," *Gene Ther. 3*:503-512, Stockton Press (1996).

Wolf, H., et al., "Epstein-Barr Virus and Its Interaction with the Host," *Intervirology 35*:26-39, S. Karger (1993).

Yang, Y., et al., "Cellular and Humoral Immune Response to Viral Antigens Create Barriers to Lung-Directed Gene Therapy with Recombinant Adenoviruses,"*J. Virol. 69*:2004-2015, American Society for Microbiology (1995).

Yang, X.W., et al., "Homologous recombination based modification in *Escherichia coli* and germline transmission in transgenic mice of a bacterial artificial chromosome," *Biotechnol. 15*:859-865, Nature Publishing Co. (1997).

Yang, X.W., et al., "BAC-mediated gene-dosage analysis reveals a role for *Zirprol* (*Ru49/Zfp38*) in progenitor cell proliferation in cerebellum and skin," *Nat. Genet. 22*:327-335, Nature Publishing Co. (1999).

Yates, J.L., et al., "Stable replication of plasmids derived from Epstein-Barr virus in various mammalian cells," *Nature 313*:812-815, Macmillan Journals Ltd. (1985).

Yee, J.K., et al., "Epitope insertion into the human hypoxanthine phosphoribosyltransferase protein and detection of the mutant protein by an anti-peptide antibody," *Gene 53*:97-104, Elsevier Science B.V. (1987).

Zhang, J. and Russell, S.J., "Vectors for cancer gene therapy," *Canc. Metast. Rev. 15*:385-401, Kluwer Academic Publishers (1996).

Zhang, Y., et al., "A new logic for DNA engineering using recombination in *Escherichia coli*," *Nat. Genet. 20*:123-128, Nature Publishing Co. (1998).

Zhang, Y., et al., "DNA cloning by homologous recombination in *Escherichia coli*," *Nat. Biotechnol. 18*:1314-1317, Nature Publishing Co. (Dec. 2000).

Ziauddin, J. and Sabatini, D.M. Microarrays of cells expressing defined cDNAs *Nature 411*:107-110, Nature Publishing Co. (May 2001).

Stavropoulos, T.A. and Strathdee, C.A, "An Enhanced Packaging System for Helper-Dependent Herpes Simplex Virus Vectors," *J. Virol. 72*:7137-7143, American Society for Microbiology (1998).

Suter, M., et al., "BAC -VAC, a novel generation of (DNA) vaccines: A bacterial artificial chromosome (BAC) containing a replication-competent, packaging-defective virus genome induces protective immunity against herpes simplex virus 1," *Proc. Natl. Acad. Sci. USA* 96:12697-12702, The National Academy of Sciences (1999).

* cited by examiner

A) Light  B) GFP  C) LDLR

*ldl-/-* a7 CHO cells + pHSV-*LDLR* (149 kb)

VIRAL DELIVERY SYSTEM FOR INFECTIOUS TRANSFER OF LARGE GENOMIC DNA INSERTS

CROSS-REFERENCE TO RELATED APPLICATIONS

This application claims the benefit of U.S. Provisional Appl. No. 60/259,697, filed Jan. 5, 2001, U.S. Provisional Appl. No. 60/287,404, filed May 1, 2001, U.S. Provisional Appl. No. 60/294,254, filed May 31, 2001, and U.S. Provisional Appl. No. 60/330,511, filed Oct. 23, 2001. The contents of the aforesaid applications are relied upon and incorporated by reference in their entirety.

STATEMENT REGARDING FEDERALLY-SPONSORED RESEARCH AND DEVELOPMENT

The U.S. Government has a paid-up license in this invention and the right in limited circumstances to require the patent owner to license others on reasonable terms as provided for by the terms of grant number NIH-PO1CA69246-05, awarded by the National Institutes of Health.

BACKGROUND OF THE INVENTION

1. Field of the Invention

The present invention relates generally to herpes simplex virus (HSV)-based amplicon vectors. More specifically, the present invention relates to a herpes simplex virus (HSV)-based amplicon vector carrying a genomic DNA fragment. The invention also relates to methods of constructing a herpes simplex virus (HSV)-based amplicon. In one aspect of the invention, a method of converting any large capacity DNA cloning vector, such as, e.g. a bacterial artificial chromosome (BAC) or a P1-artificial chromosome (PAC) clone, into a herpes simplex virus (HSV) amplicon or hybrid HSV amplicon is provided. This method can be accomplished by using recombination, such as site-specific or homologous recombination, or ligation. According to this aspect of the invention, genomic DNA inserts within the large capacity DNA cloning vector can be delivered by infectious transfer to a target cell, and expressed, in vitro and in vivo. The present invention also relates to a system for the rapid creation of viral vectors carrying transgenes of interest. This aspect of the invention is accomplished through site-specific recombination between: (a) a large-capacity cloning vector carrying a viral genome, and (b) a transfer vector containing the transgene of interest. The present invention also relates to expression-ready genomic DNA libraries and methods of isolating a genomic DNA clone encoding a gene product with a preselected function.

2. Background Art

The terms "gene transfer" and "gene therapy" have been used to describe a variety of methods for delivering genetic material to a cell using viral or non-viral based vector systems. Substantial attention has been given to human gene therapy. The transfer of genetic material to a cell may one day become one of the most important forms of medicine. A variety of public and private institutions now participate in research and development related to the use of genetic material in therapeutic applications. Hundreds of human gene transfer protocols are being conducted at any given time with the approval of the Recombinant DNA Advisory Committee (RAC) and the National Institutes of Health (NIH). Most of these protocols focus on therapy, while others involve marking and non-therapeutic applications. The therapeutic protocols are primarily concerned with infectious diseases, monogenic diseases, and cancer. Gene-based therapies are now expanding into fields such as cardiovascular disease, autoimmune disease, and neurodegenerative disease. The availability of an efficient gene delivery and expression system is essential to the success and efficacy of gene-based therapy.

One method of delivering a gene of interest to a target cell is by using a viral-based vector. Techniques for the formation of vectors or virions are generally described in "Working Toward Human Gene Therapy," Chapter 28 in *Recombinant DNA,* 2nd Ed, Watson, J. D. et al., eds., New York: Scientific American Books, pp. 567–581 (1992). An overview of viral vectors or virions that have been used in gene therapy can be found in Wilson, J. M., *Clin. Exp. Immunol.* 107(Suppl. 1):31–32 (1997), as well as Nakanishi, M. *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA or DNA.

Specific examples of viral vector systems that have been utilized in the gene therapy art include: retroviruses (Vile, R. G., supra; U.S. Pat. Nos. 5,741,486 and 5,763,242); adenoviruses (Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763,217; Chase, M., et al., *Nature Biotechnol.* 16:444–448 (1998)); parvovirus (Shaughnessy, E., et al., *Semin Oncol.* 23:159–171 (1996)); and reticuloendotheliosis virus (Donburg, R., *Gene Therap.* 2:301–310 (1995)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M. *Crit. Rev. Therapeu. Drug Carrier Systems* 12:263–310 (1995); Zhang, J., et al., *Cancer Metastasis Rev.* 15:385–401 (1996); Jacoby, D. R., et al., *Gene Therapy* 4:1281–1283 (1997)). Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,601,818, and WO 95/06486.

The viral vectors mentioned above have advantages and disadvantages. For example, retroviruses have the ability to infect cells and have their genetic material integrated into the host cell with high efficiency. The development of a helper virus free packaging system for retrovirus vectors was a key innovation in the development of this vector system for human gene therapy. Retroviral helper virus free packaging systems generally employ the creation of a stable producer cell line that expresses a selected vector.

On a down side, however, numerous difficulties with retroviruses have been reported. For example, most retroviral vectors are not capable of gene transfer to postmitotic (nondividing) cells and are thus not applicable to the nervous system because most of the cells in the adult nervous system, especially neurons, are quiescent or postmitotic. In addition, outbreaks of wild-type virus from recombinant virus-producing cell lines have also been reported.

Difficulties have been noted with other viral vectors as well. Adenovirus vectors can only support limited long-term (2 months) gene expression, they appear to be gradually lost from neural cells, and moreover, they can cause both cytopathic effects and an immune response (Le Gal La Salle, G., et al., *Science* 259:988–990 (1993); Davidson et al., *Nat. Genet.* 3:219–223 (1993); Yang, Y., et al., *J. Virol.* 69:2004–2015 (1995)). Adeno-associated virus vectors cause minimal cytopathic effects and can support at least some gene expression for up to 4 months, but gene transfer is inefficient and these vectors can accept only ~4 kb of foreign DNA (Kaplitt, M. G., et al., *Nat. Genet.* 8:148–154 (1994)).

The herpesviruses are a family of human viruses which include cytomegalovirus (CMV; 230 kb genome size), Epstein-Barr virus (EBV; 172 kb) and Herpes Simplex virus Types 1 and 2 (HSV-1 and 2; 152 kb). EBV and HSV-1 in particular have features which make them attractive as gene delivery vectors. EBV has a mechanism of prolonged extra-chromosomal (episomal) maintenance in long-lived memory B-cells using the interaction of the latent origin of replication (oriP) and the viral protein EBV nuclear antigen-1 (EBNA-1) (Wolf, H., et al., *Intervirology* 35:26–39 (1993)). Plasmid vectors incorporating oriP and an expression cassette for EBNA-1 are maintained in certain cell types for prolonged periods (Yates, J. L., et al., *Nature* 313:812–815 (1985)).

Vectors based on herpes simplex virus (HSV), and especially HSV-1, have shown considerable promise as potent gene delivery vehicles for several reasons: the virus has a very large genome and thus can accommodate large amounts of foreign DNA (greater than 30 kb), the virus can persist long-term in cells (they establish latency), and can efficiently infect many different cell types, including post-mitotic neural cells (Breakefield, X. O., et al., "Herpes Simplex Virus Vectors for Tumor Therapy," in *The Internet Book of Gene Therapy: Cancer Gene Therapeutics*, R. E. Sobol and K. J. Scanlon, eds. Appleton and Lange, Stamford, Conn., pp. 41–56 (1995); Glorioso, J. C., et al., "Herpes Simplex Virus as a Gene-Delivery Vector for the Central Nervous System," in Viral Vectors: *Gene Therapy and Neuroscience Applications*, M. G. Kaplitt and A. D. Loewy, eds., Academic Press, New York, pp. 1–23 (1995)).

The recent manipulation of CMV, EBV and HSV-1 in bacteria (Messerle, M., et al., *Proc. Natl. Acad. Sci. USA* 94:14759–14763 (1997); Delecluse, H. J., et al., *Proc. Natl. Acad. Sci. USA* 95:8245–8250 (1998); Saeki, Y., et al., *Hum. Gene Ther.* 9:2787–2794 (1998)) is greatly assisting their progress as gene delivery vectors, and has led to the development of helper virus-free packaging systems for EBV and HSV-1 (Delecluse, H. J., et al., *Proc. Natl. Acad. Sci. USA* 95:8245–8250 (1998); Saeki, Y., et al., *Hum. Gene Ther.* 9:2787–2794 (1998)). Infectious amplicon vectors, which incorporate a viral origin of replication and a viral packaging signal into a bacterial plasmid, have been developed for both EBV and HSV-1.

HSV-1 amplicons carrying the $ori_s$ replication origin and the pac signal have been widely used for gene delivery both in vivo and in vitro (Spaete, R. R., and Frenkel, N., *Cell* 30:295–304 (1982); Spaete, R. R., and Frenkel, N., *Proc. Natl. Acad. Sci. USA* 82:694–698 (1985); Geller, A. I., and Breakefield, X. O., *Science* 241:1667–1669 (1988); Sena-Esteves, M., et al., *Mol. Ther.* 2:9–15 (2000)). HSV amplicon vectors are one of the most versatile, most efficient, and least toxic, and have the largest transgene capacity of the currently available viral vectors. HSV-1 amplicon vectors can support some gene expression for up to one year (During, M. J., et al., *Science* 266:1399–1403 (1994)).

EBV amplicons carrying both the latent (oriP) and lytic (oriLyt) viral origins of replication together with the Terminal Repeats (TR) necessary for viral packaging have been used for gene transfer and expression in B-cell lines (Hammerschmidt, W., and Sugden, B., *Cell* 55:427–433 (1988); Hammerschmidt, W., and Sugden, B., *Nature* 340:393–397 (1989); Banerjee, S., et al., *Nature Med.* 1:1303–1308 (1995)). In addition, the large size of the herpesvirus genomes confers the potential for the delivery of very large transgenes. It is believed that the largest insert delivered by an HSV-1 amplicon previous to our study was 40 kb, and no expression from the insert was shown (Wang, X., et al., *BioTechniques* 27:102–106 (1999)).

The particular advantages of HSV-1 and EBV may be combined in a hybrid vector (Wang, S., et al., *Gene Ther.* 4:1132–1141 (1997)). HSV-1/EBV hybrid vectors packaged as HSV-1 amplicons are promising tools for gene delivery because: (i) HSV-1 has a high transgene capacity of approximately 150 kb; (ii) high-titre amplicon stocks can be produced by helper virus-free packaging systems; and (iii) the resulting virion particles have a broad cell tropism across a wide range of species. It is believed that HSV-1 is unique in being able to combine all these features. The addition of the EBV mechanism of episome retention allows long term persistence of the recircularized vector. The inclusion of a large genomic insert would further ensure such an episome can replicate in rodent cells (Wohlgemuth, J. G., et al., *Gene Ther.* 3:503–512 (1996)), further increasing the vector's utility in disease models.

Because HSV-1 encodes many toxic functions, improvements on the amplicon system have been targeted primarily at reducing the risk associated with the helper virus. First, replication-competent HSV-1, initially used as helper virus, was replaced by a temperature-sensitive (ts) mutant of HSV-1 (HSV-1 tsK; Preston, C., *J. Virol.* 29:257–284 (1979)). This mutant encodes a temperature-sensitive form of the essential HSV-1 infected cell protein (ICP) 4, allowing HSV-1 replication to proceed at 31° C., but not at 37° C. Amplicons packaged at 31 ° C. in the presence of HSV-1 tsK were successfully used to transfer the *E. coli* lacZ gene into primary cultures of rat neural cells (Geller, A. I. and Breakefield, X. O., *Science* 241:1667–1669 (1988)). Because the infection was performed at 37° C., the lytic cycle of the HSV-1 tsK helper virus present in the vector stock was blocked and cell damage was limited. Although replication of HSV-1 tsK was inhibited at the restrictive temperature, the expression of other viral genes caused cytopathic effects. Moreover, reversion to wild type (wt) HSV-1 occurred at a relatively high frequency.

To counter these problems, replication-defective mutants of HSV-1 were then used as helper viruses (Geller, A.I. et al., *Proc. Natl. Acad. Sci. USA* 87:8950–8954 (1990); Lim, F., et al., *BioTechniques* 20:458–469 (1996)). These mutants carry deletions in genes that are essential for virus replication, but they can support amplicon packaging in cells that complement the missing functions. In general, deletion-mutant packaging systems produce relatively high amplicon vector titers ($10^{6-10^7}$ transducing units per ml (t.u./ml)), a ratio of transducing vector units to helper virus of up to 1, and low levels of revertants with wt HSV-1 phenotype ($<10^{-7}$ plaque forming units (PFU), per ml; Lim, F., et al., supra). However, many problems associated with the presence of helper virus in amplicon stocks still remained, including: (i) pronounced cytopathic effects and immune responses caused by gene expression from the helper virus; (ii) interactions between the helper virus and endogenous viruses; (iii) reversion of the helper virus to wt HSV-1; and (iv) disregulation of transgene expression by virus proteins.

Many of these problems have been overcome by the development of a packaging system for herpes virus vectors that was free of helper virus (Fraefel, C., et al., *J. Virol.* 70:7190–7197 (1996); International Patent Publication WO 97/05263, published February 13, 1997)). This system utilizes transient co-transfection of amplicon DNA with a set of five cosmids that overlap and represent the entire HSV-1 genome, but which are mutated to delete the DNA cleavage/ packaging (pac) signals. Cunningham, C. and Davison, A. J., *Virology* 197:116–124 (1993), had demonstrated previously that after transfection into cells, an overlapping HSV-1 cosmid set can produce infectious virus progeny. By deleting the pac signals and making a pacminus helper virus genome, HSV-1 genomes that are potentially reconstituted from the cosmids via homologous recombination, are not packageable, but can still provide all the helper functions required for the replication and packaging of the co-transfected amplicon DNA. The resulting vector stocks are, therefore, virtually free of detectable helper virus and have titers of $10^6$–$10^7$ t.u./ml of culture medium. Because of minimal sequence homology between the cosmids and the amplicon DNA ($ori_s$; 0.2–1 kb), the formation of a packageable and replication-competent HSV-1 genome is possible, but requires 6 recombination events, and is therefore very rare. Amplicon vector stocks, produced by using the helper virus-free packaging system, can efficiently transduce many different cell types, including neural cells and hepatocytes in culture and in vivo, while causing minimal to no cytopathic effects (Fraefel, C., et al., *J. Virol.* 70:7190–7197 (1996); Fraefel, C., et al., *Mol. Med.* 3:813–825 (1997); Fraefel, C., et al., "HSV-1 Amplicon" in *Gene Therapy for Neurological Disorders and Brain Tumors*, E. A. Chiocca and X. O. Breakefield, eds., Humana Press, Totowa, pp. 63–82 (1998); Johnston, K. M., et al., *Hum. Gene Ther.* 8:359–370 (1997); Aboody-Guterman, K. S., et al., *NeuroReport* 8:3801–3808 (1997)).

Even more recently, the helper virus-free herpes amplicon packaging system has been simplified further by reducing the number of clones representing the HSV-1 genome to a single clone (International Patent Publication WO 0034497; Saeki et al., *Human Gene Therapy* 9:2787–2794 (1998)). In this simplified system, a packaging vector comprising a single clone (i.e., a BAC containing the entire HSV-1 genome) was used as "helper virus."

Most current viral vectors have a transgene capacity limited to the delivery of cDNA-based expression cassettes, often driven by strong heterologous viral promoters. In contrast, the delivery of a genomic DNA transgene driven by the native promoter, flanked by the regulatory regions and including introns, offers the potential for investigating and exploiting the physiological control of gene expression (Li, Q., et al., *Trends Genet.* 15:403–408 (1999); Blackwood, E. M. and Kadonaga, J. T., *Science* 281:60–63 (1998)). Many studies have demonstrated the advantages of using genomic DNA in cell culture and transgenic animal models (Yang, X. W., et al., *Nature Biotechnol.* 15:859–865 (1997); Wade-Martins, R., et al., *Nature Biotech* 18:1311–1314 (December 2000); Schiedner, G., et al., *Nature Genet.* 18:180–183 (1998); Peterson, K. R., et al., *Proc. Natl. Acad. Sci. USA* 90:11207–11211 (1993)). Viral vectors are an efficient means of delivering genes to cells, but the size of most genomic loci precludes their use in current viral systems.

The development of bacterial artificial chromosomes (BACs) (Shizuya, H., et al., *Proc. Natl. Acad. Sci. USA* 89:8794–8797 (1992)) and P1-artificial chromosomes (PACs)(Ioannou, P. A., et al., *Nature Genet.* 6:84–89 (1994)) has greatly aided physical mapping projects and genomic sequencing. BACs and PACs have many advantages over yeast artificial chromosomes (YACs) for cloning large DNA inserts (Monaco, A. P., and Larin, Z., Trends Biotech. 12:280–286 (1994)), including the ease of preparation of microgram quantities of vector. Nonetheless, the use of all three vectors in gene expression studies is restricted by the difficulty of transferring and retaining intact pieces of genomic DNA >100 kb in human cells. As a result of the human genome sequencing projects, virtually the entire human genome is now covered by BAC contigs, which makes BACs an excellent platform for functional genomics studies (Simon, M. I., *Nature Biotechnol.* 15:839 (1997)).

Gene expression from BACs and PACs has been demonstrated in cell culture systems (Wade-Martins, R., et al., *Nature Biotech* 18:1311–1314 (December 2000); Compton, S. H., et al., *Gene Ther.* 7:1600–1605 (2000); Kim, S. Y., et al., *Genome Res.* 8:404–412 (1998)) and in transgenic animal models (Antoch, M. P., et al., *Cell* 89:655–667 (1997); Yang, X. W., et al., *Nature Genet.* 22:327–335 (1999)). Wade-Martins et al. has developed a large insert shuttle vector for gene expression in human cells based on a fusion of the BAC and EBV episome technologies (Wade-Martins, R., et al., *Nature Biotech* 18:1311–1314 (December 2000); Wade-Martins, R., et al., *Nucleic Acids Res.* 27:1674–1682 (1999)). The vector was used for complementation of a cell culture phenotype by a genomic DNA transgene retained in human cells as an EBV-based episome (Wade-Martins, R., et al., *Nature Biotech* 18:1311–1314 (December 2000)). Extrachromosomal maintenance of the construct prevented DNA rearrangement often seen on construct integration. The vector described by Wade-Martins, supra, is based solely on EBV features, but not HSV-1. Moreover, it is not an infectious viral system. It can only be transferred to mammalian cells by physical transfection, which is much less efficient than viral transfer. Even if the Wade-Martins vector were to be turned into an infectious EBV-based vector, it would be severely limited by the problems of an EBV system, namely (i) the inability to make high titre virus and (ii) a very narrow range of cell infectivity.

Westphal, E. M., et al., *Human Gene Therapy* 9:1863–1873 (September 1998) and international Patent Publication WO 00/12693 to Vos et al. relate to a vector system for shuttling large genomic inserts from preexisting BAC or PAC libraries into human cells. The system utilizes a hybrid BAC-HAEC (human artificial episomal chromosome), which contains an F-based replication system as in BAC and the EBV oriP, for replication in human cells. Transcription of the human beta-globin gene (185 kb) was observed in vitro.

U.S. Pat. No. 6,143,566 to Heintz et al. relates to targeted BAC modification. This patent teaches a method for directly modifying an independent origin based cloning vector (such as a BAC, in one specific embodiment) in recombination deficient host cells, including generating deletions, substitutions, and/or point mutations in a specific gene contained in the cloning vector. The modified cloning vector may be used to introduce a modified heterologous gene into a host cell. In one Example presented, a modified BAC was inserted into a murine subject animal, and in vivo heterologous gene expression demonstrated. The methodology of this invention involves homologous recombination of the cloning vector with a conditional replication shuttle vector in a RecA.sup.—host cell, wherein the conditional replication shuttle vector encodes a RecA-like protein. In a preferred embodiment, the vector is a BAC that has undergone homologous recombination with the temperature sensitive shuttle vector pSV1.RecA.

Clearly, there is a need in the art to simplify and enhance viral gene delivery systems for large capacity DNA cloning vectors, such as, e.g., BACs and PACs, so that genomic DNA inserts (and in particular large genomic DNA inserts) within the large capacity DNA cloning vector can be more easily transferred by infection into cells (in vitro and in vivo), in order to study and exploit gene expression and function. Since, as a result of the efforts of the Human Genome Project, the human genome is now covered by BAC contigs (i.e., BACs comprising overlapping genomic fragments), this vector system has utility for the efficient delivery of large genomic transgenes in functional genomics studies and gene therapy applications.

BRIEF SUMMARY OF THE INVENTION

Accordingly, the present invention overcomes the disadvantages of the prior art by providing a herpes simplex virus (HSV)-based amplicon vector carrying a genomic DNA fragment. The invention further provides methods of constructing a herpes simplex virus (HSV)-based amplicon. The HSV-based amplicon vectors of the present invention facilitate the delivery of genomic DNA to a target cell.

In one aspect of the invention, an HSV-based amplicon vector carrying a genomic DNA fragment is provided comprising: (a) a large capacity cloning vector, (b) a herpes virus origin of replication, (c) a herpes virus cleavage/packaging signal, and (d) a genomic DNA fragment; wherein said HSV-based amplicon vector can infect and deliver said genomic DNA to a target cell.

In another aspect of the invention, an improved and simplified method is provided for converting large capacity DNA cloning vectors, such as, e.g. a bacterial artificial chromosome (BAC) clone or a P1-artificial chromosome (PAC) clone into herpes simplex virus (HSV)-based amplicons, so that large genomic transgenes within the large capacity DNA cloning vector can be more efficiently delivered to a target cell, and expressed in vitro or in vivo.

More specifically, in an exemplified embodiment of the present invention, loxP/cre-mediated recombination was used to convert BAC or PAC clones into a hybrid HSV/EBV amplicon. In this way, two large genomic DNA inserts within the large capacity DNA cloning vector were delivered by infectious transfer to target cells, and expressed, in vitro. Since the present method involves an infectious viral system, rather than the much less efficient process of physical transfection, the present method is capable of delivering intact vector more efficiently and easily than those shown in the art.

Thus, the present invention provides a method of converting a large capacity cloning vehicle containing genomic DNA into a herpes simplex virus (HSV)-based amplicon, such that said HSV-based amplicon can infect and deliver said genomic DNA to a cell, comprising recombining said HSV-based amplicon vector with said large capacity cloning vehicle. Site-specific recombination, homologous recombination, or ligation may be used.

The present invention also provides a method of constructing a HSV-based amplicon carrying a genomic DNA fragment comprising subcloning said genomic DNA fragment into a cloning vehicle comprising: (a) a large capacity cloning vector, (b) a herpes virus origin of replication, and (c) a herpes virus cleavage/packaging signal; such that said HSV-based amplicon can infect and deliver said genomic DNA to a target cell.

The present invention utilizes a large capacity cloning vector, such as a BAC or a PAC. Although a BAC or PAC is a particularly preferred large capacity cloning vector, other large capacity cloning vectors known to those skilled in the art can also be used in the present invention. These include, e.g., cosmids, yeast artificial chromosomes (YACS), mammalian artificial chromosomes (MACS), human artificial chromosomes, or viral-based vectors, such as, e.g., CMV, EBV, or baculovirus.

The present method also utilizes a herpes simplex virus (HSV)-based amplicon. The HSV-based amplicon is derived from an alpha herpesvirus such as herpes simplex virus (HSV-1 or HSV-2). HSV-1 is a particularly preferred herpes virus amplicon. Genetic elements from other herpes viruses, such as Epstein-Barr virus (EBV), may be added to the amplicon construct in addition to the components from HSV-1. That is, the HSV-based amplicon that is used in the method of the invention may comprise an HSV-1 amplicon, alone, or as a component of an HSV-1 hybrid amplicon (e.g., EBV could be used together with HSV). The hybrid HSV-1/EBV amplicon is a particularly preferred herpes simplex virus-based amplicon. Other viral vector systems may be used in conjunction with the present invention, including systems based on cytomegalovirus (CMV), EBV, or baculovirus.

The method of the invention is preferably accomplished by using site-specific recombination between the large capacity cloning vector and the HSV-based amplicon. In a very preferred embodiment, loxP/cre-mediated recombination is used. Alternatively, recombination can be accomplished using homologous recombination or ligation, or any other recombination method known to those skilled in the art.

The genomic DNA contained in the BAC/PAC can be human or nonhuman, e.g., animal, mammalian, avian, mouse, amphibian, and the like. The genomic DNA contained in the BAC or PAC library may contain a gene that encodes a protein, for example, a therapeutic protein. Specific knowledge of a gene's presence or function, however, is not necessary in this method, as functional genomic assays can be performed to determine the presence or function of a gene in a particular genomic insert.

Alternatively, in another embodiment, the genomic DNA may contain regulatory or controlling DNA sequences, including promoter regions, and thus may not code for a protein.

Also, the genomic DNA may comprise human or mammalian centromeric DNA for the creation of human or mammalian artificial chromosomes.

In another aspect of the invention, a system is provided that allows for the rapid creation of viral vectors, e.g., herpes simplex virus (HSV) vectors or adenovirus (Ad) vectors, carrying transgenes of interest.

In an exemplary embodiment of this aspect of the invention, two components are provided. The first component (component 1) is a large capacity cloning vector or plasmid carrying a viral genome. The large capacity cloning vector may be a BAC or PAC or any other suitable vector or plasmid known by persons skilled in the art. Preferably, the vector or plasmid backbone sequence is flanked by two non-identical site-specific recombinase recognition sequences; e.g., loxP (recognized by the Cre recombinase) and FRT (recognized by the Flp recombinase). Any recombination system may be used in the present invention.

Additionally, the first component may also carry a marker gene such as green fluorescent protein (GFP) or enhanced green fluorescent protein (EGFP).

The second component (component 2) is a transfer vector carrying a transgene of interest. The transfer vector backbone can be any suitable vector known by persons skilled in the art. In a preferred embodiment, the transfer vector also carries a conditional origin of replication. Preferably, the transgene of component 2 is flanked by two different site-specific recombinase recognition sequences corresponding to those found in component 1.

According to this aspect of the invention, a viral vector carrying a transgene of interest can be created by first co-transforming an appropriate bacterial cell with the viral genome-carrying vector or plasmid (component 1) and the transfer vector (component 2). Through enzyme-mediated site-specific recombination (or any other recombination technique known to those skilled in the art), a precursor construct is created from the two components. In a preferred embodiment, the site-specific recombination event occurs between the FRT sites of components 1 and 2 via Flp recombinase. The bacterial cells harboring the precursor can be stored and maintained as a bacterial stock for further modification.

Next, according to this aspect of the invention, the precursor plasmid is isolated from the bacterial cell and then transfected into a host cell. The host cell can be a VERO cell, a 293 cell, or any other appropriate host cell known by those in the art. Following transfection, the prokaryotic backbone or other unwanted DNA sequence may be removed from the precursor through enzyme-mediated site-specific recombination (or any other recombination technique known to those skilled in the art). In a preferred embodiment, the site-specific recombination event is Cre-mediated recombination that occurs between the loxP sites found on the precursor, thereby creating a viral vector carrying the transgene of interest. Virus particles containing the resultant vector can then be obtained from the host cell.

In another aspect of the invention, an expression-ready genomic DNA library is provided for use in functional genomics.

In an exemplary embodiment of this aspect of the invention, the library is comprised of a plurality of vectors, each vector comprising: (a) a large capacity cloning vector, (b) a herpes virus origin of replication, (c) a herpes virus cleavage/packaging signal, and (d) a genomic DNA fragment. The large capacity cloning vector can be a BAC or PAC or any other suitable vector or plasmid known by persons skilled in the art. The herpes virus origin of replication, and the herpes virus cleavage/packaging signal, can be derived from HSV-1.

According to this aspect of the invention, the vectors of the library are capable of being propagated within bacterial cells and are also capable of being packaged into infectious particles. The vectors can be packaged into infectious particles by any method known by those skilled in the art. In one embodiment, the vectors are packaged using a helper virus free packaging system.

The genomic DNA fragment of this aspect of the invention can be derived from any species of interest, including human, mouse and rat.

In another aspect of the invention, a method is provided for isolating a genomic DNA clone encoding a gene product with a preselected function.

According to this aspect of the invention, an infectious, expression-ready genomic DNA library is obtained. The library is comprised of a plurality of vectors, each vector comprising: (a) a large capacity cloning vector, (b) a herpes virus origin of replication, (c) a herpes virus cleavage/packaging signal, and (d) a genomic DNA fragment.

According to this aspect of the invention, the vectors of the library are packaged into infectious particles. The vectors can be packaged into infectious particles by any method known by those skilled in the art. In one embodiment, the vectors are packaged using a helper virus free packaging system.

The infectious particles packaged according to this aspect of the invention are then used to infect model cells. Model cells can be any cells that permit the identification of the preselected function. Exemplary model cells include human or mouse cells or primary cells. Individual infected cells are identified that exhibit a phenotype indicative of the preselected function, and the genomic DNA fragment of the library vector is isolated. The nucleotide sequence of the isolated genomic DNA fragment can then be determined.

It is to be understood that both the foregoing general description and the following detailed description are exemplary and explanatory and are intended to provide further explanation of the invention as claimed.

BRIEF DESCRIPTION OF THE FIGURES

FIG. 1A depicts an overview of the strategy to rapidly obtain and analyze a genomic DNA sequence using the amplicon system.

FIG. 1B depicts a size series of HSV-1/EBV hybrid amplicons created by fitting BAC and PAC constructs with pEHHG, using cre-mediated recombination at the loxp site on the BAC/PAC library vector. The plasmid pHSV-143 (also called pHSV-HPRT) contains the complete genomic DNA locus of the human hypoxanthine phosphoribosyl-transferase (HPRT) gene.

The arrow indicates the direction of transcription of the HPRT locus.

Figure 1:
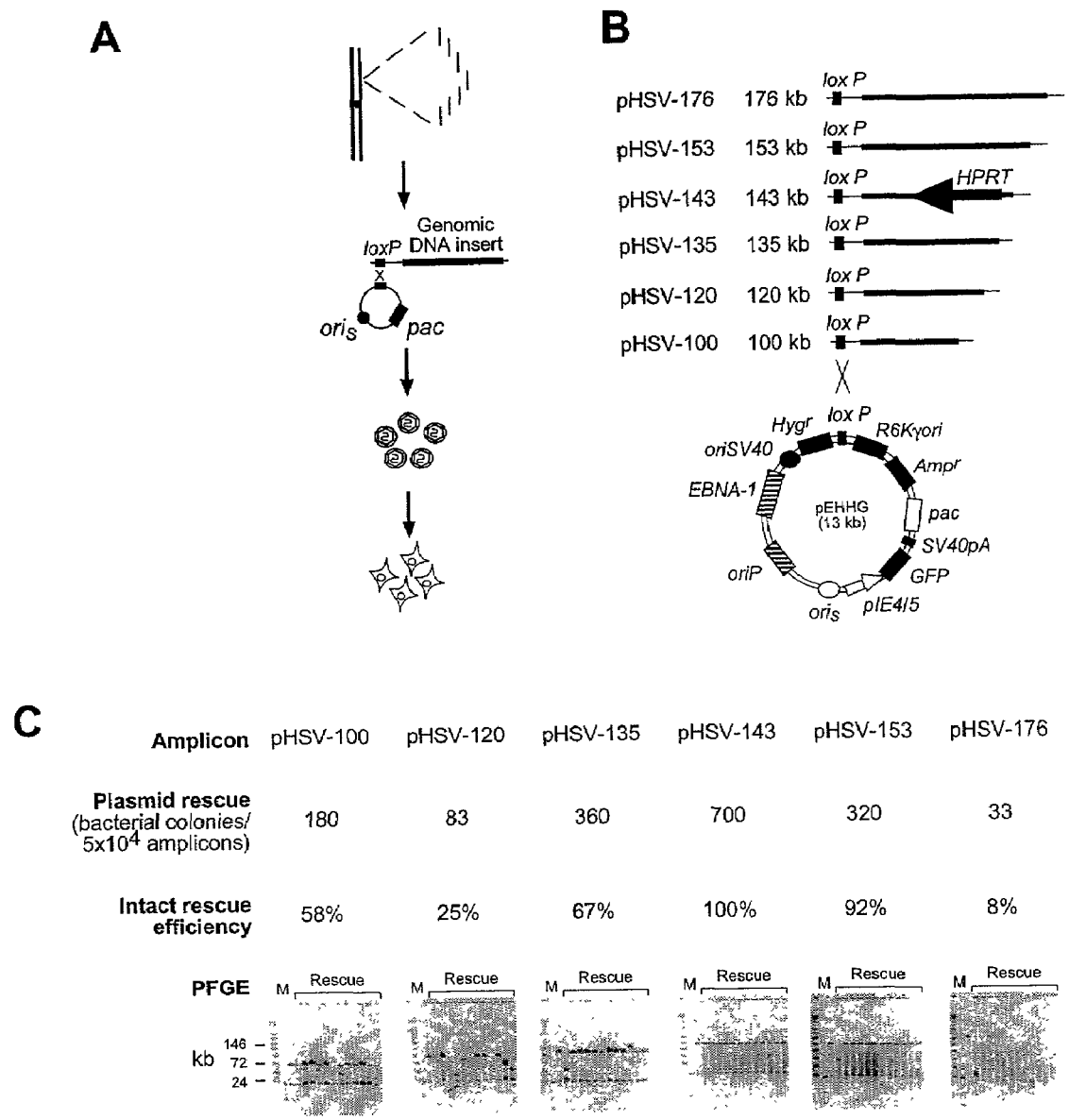
FIGS. 1A–1C show that the high capacity HSV-1 amplicon system delivers intact genomic DNA inserts >100 kb.

FIG. 1C depicts plasmid rescue of the amplicon series from MRC-5V2 cells 48 hours post-infection. Plasmid DNA was prepared from 12 bacterial colonies from each rescue assay, digested with NotI, and analysed by pulsed field gel electrophoresis (PFGE). The proportion of bacterial colonies containing intact rescued amplicon is given for each member of the size series.

Figure 2:
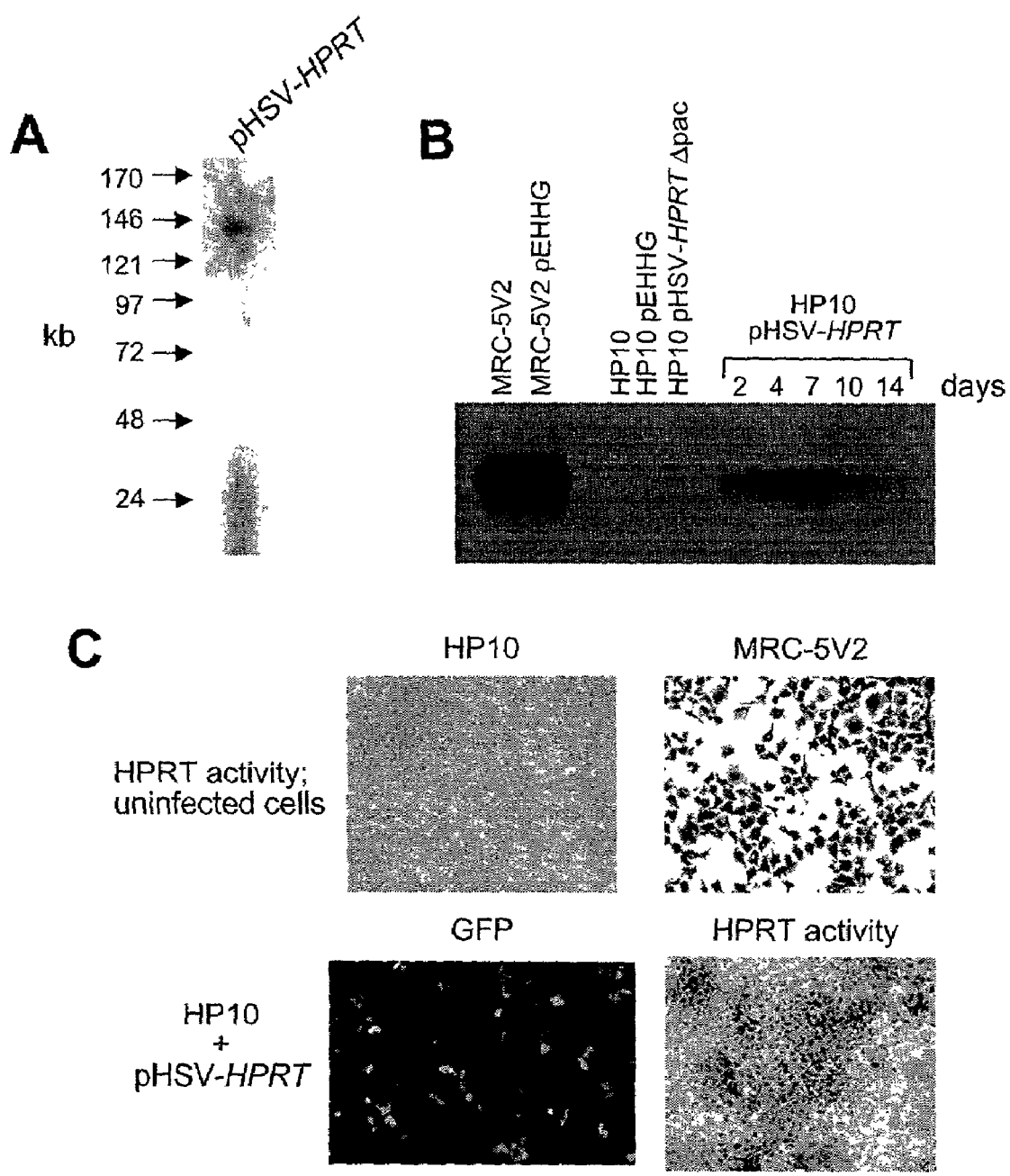

FIGS. 2A–2C show that the genomic DNA insert present within pHSV-HPRT is intact within the virion and is functional upon delivery.

FIG. 2A shows that the pHSV-HPRT virion contains DNA of 143 kb, the correct size of pHSV-HPRT.

FIG. 2B depicts an HPRT activity gel showing that the HPRT genomic DNA transgene present on the 115 kb insert of pHSV-HPRT (pHSV-143) is functional following infectious delivery. HP10 cells were infected with pHSV-HPRT, pHSV-HPRTΔpac or empty amplicon pEHHG at an MOI of ~1 and HPRT activity was assayed by an activity gel assay at several time-points post-infection. Fifteen micrograms of protein were loaded in each lane.

FIG. 2C depicts HPRT activity (bottom right panel) and GFP expression (bottom left panel) in HP10 cells seventy two hours post-infection with pHSV-HPRT. HPRT activity was detected by autoradiography, and cells were counter-stained using hematoxylin and eosin. The upper panels show negative (upper left) and positive (upper right) controls for the HPRT autoradiography assay.

Figure 3:
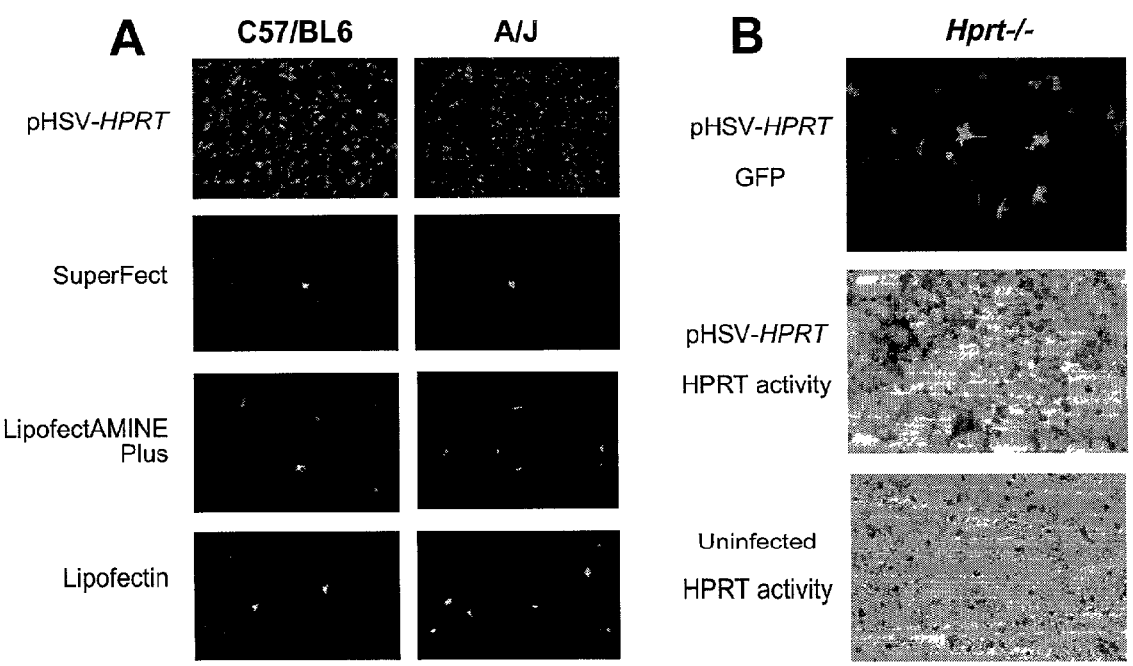

FIGS. 3A–3B compare infection and transfection of primary mouse hepatocyte cultures by pHSV-HPRT.

FIG. 3A shows infection of primary mouse hepatocyte cultures is more efficient at pHSV-HPRT delivery than transfection. Sub-confluent layers of primary cultures derived from either C57/BL6 or A/J mouse strains were infected with pHSV-HPRT amplicon at an MOI of 1, or were transfected with pHSV-HPRT plasmid using commercially available reagents according to the manufacturers instructions. The photographs show GFP expression in representative areas of culture forty-eight hours post-infection or transfection.

FIG. 3B shows infection of pHSV-HPRT to primary mouse hepatocyte cultures derived from Hprt-/- mice results in the delivery of a functional HPRT transgene. The upper panel shows GFP expression, and the lower two panels show HPRT activity as assayed by autoradiography following incubation of the cells in medium containing [$^3$H]-hypoxanthine.

FIGS. 4A–4D depict an analysis of three clonal cell lines carrying episomal pHSV-HPRT following infection and selection for two months of continuous culture.

Figure 4:
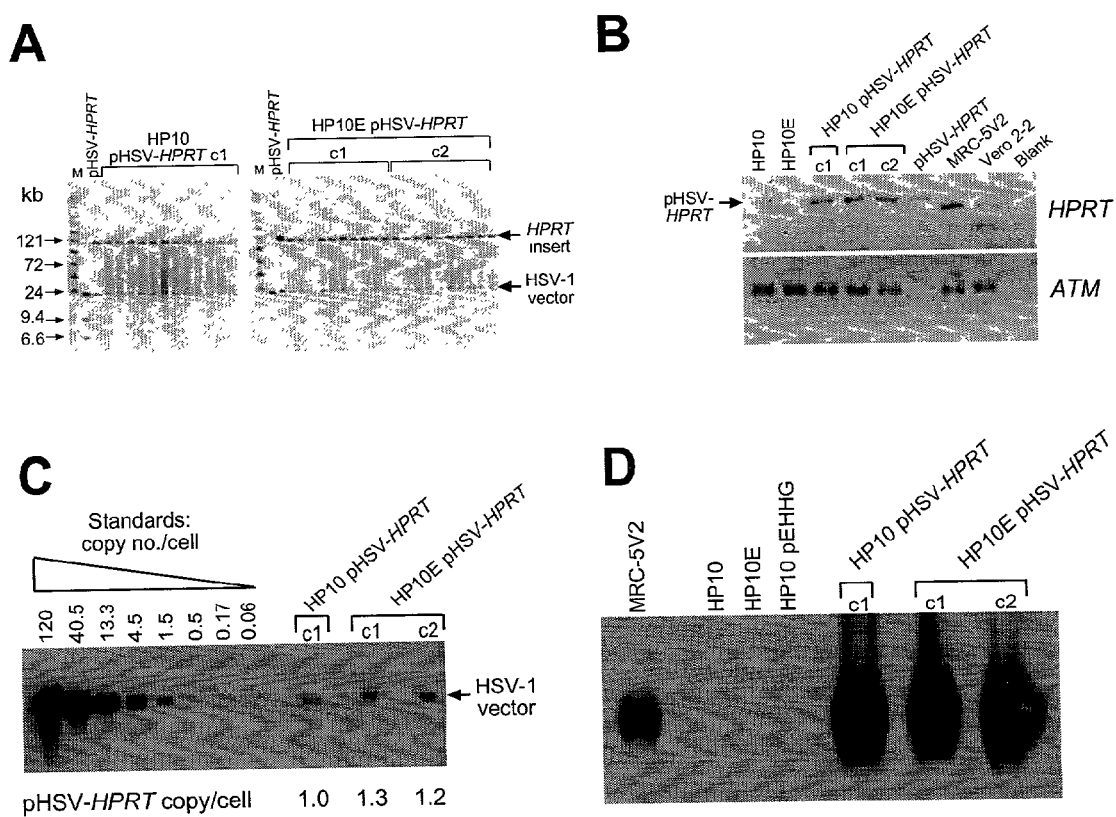

FIG. 4A shows that plasmid rescue from all three clones yielded only intact episome.

FIG. 4B depicts PCR analysis of HUMHPRTB, a polymorphic marker within intron 3 of the human HPRT locus. Genotype analysis of the three pHSV-HPRT clonal cell lines shows the HPRT allele present on pHSV-HPRT has been transferred to the transduced HP10 lines.

FIG. 4C depicts copy number determination of pHSV-HPRT for the three clonal lines by quantitative Southern blotting. This revealed that the episomal vector was present at approximately 1 copy/cell in the lines under hygromycin selection.

FIG. 4D depicts an HPRT activity gel for the three clonal lines. All three clones strongly express the human HPRT enzyme, whereas a population of HP10 cells carrying only pEHHG has no detectable HPRT activity.

FIGS. 5A–5F demonstrate construction and delivery of infectious BAC vectors carrying the human low density lipoprotein receptor (LDLR) gene.

Figure 5:
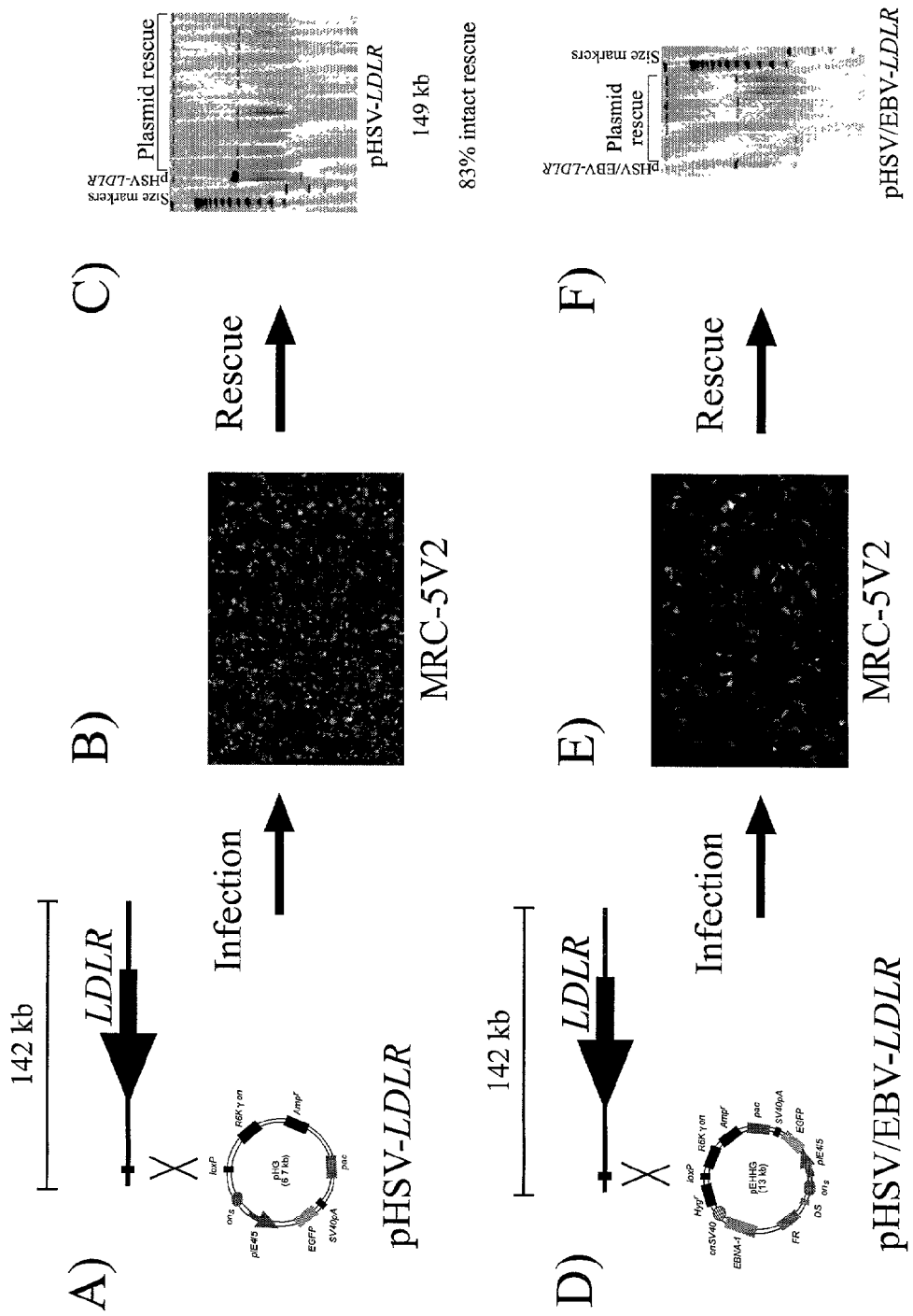

FIG. 5A depicts the conversion of the LDLR BAC clone into a HSV-1 based amplicon vector (pHSV-LDLR).

FIG. 5B shows efficient infectious delivery of the 149 kb pHSV-LDLR into the MRC-5V2 human fibroblast cell line, by assaying GFP expression.

FIG. 5C shows the result of the plasmid rescue from the MRC-5V2 cells. The pHSV-LDLR vector is rescued intact with a 75% efficiency.

FIG. 5D depicts the conversion of the LDLR BAC clone into a HSV1/EBV based amplicon vector (pHSV/EBV-LDLR).

FIG. 5E shows efficient infectious delivery of the 156 kb pHSV/EB-VLDLR into the MRC-5V2 human fibroblast cell line, by assaying GFP expression.

FIG. 5F shows the result of the plasmid rescue from the MRC-5V2 cells. The pHSV/EBV-LDLR vector is rescued intact with a 57% efficiency.

Figure 6:
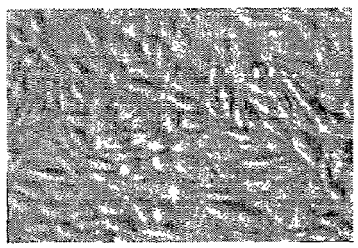
Figure 6:
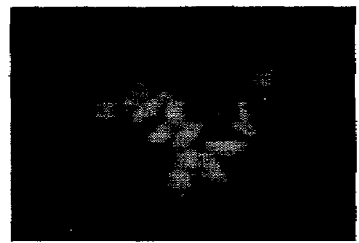
Figure 6:
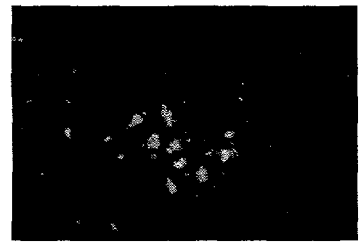

FIGS. 6A–6C demonstrate expression of the LDLR gene from the pHSV-LDLR vector delivered by infection in the CHO idlr-/- a7 cell line.

FIG. 6A shows a phase contrast image of the cells.

FIG. 6B shows GFP expression from pHSV-LDLR.

FIG. 6C shows uptake of DiI-LDL, a fluorescently-labelled form of LDL.

Figure 7:
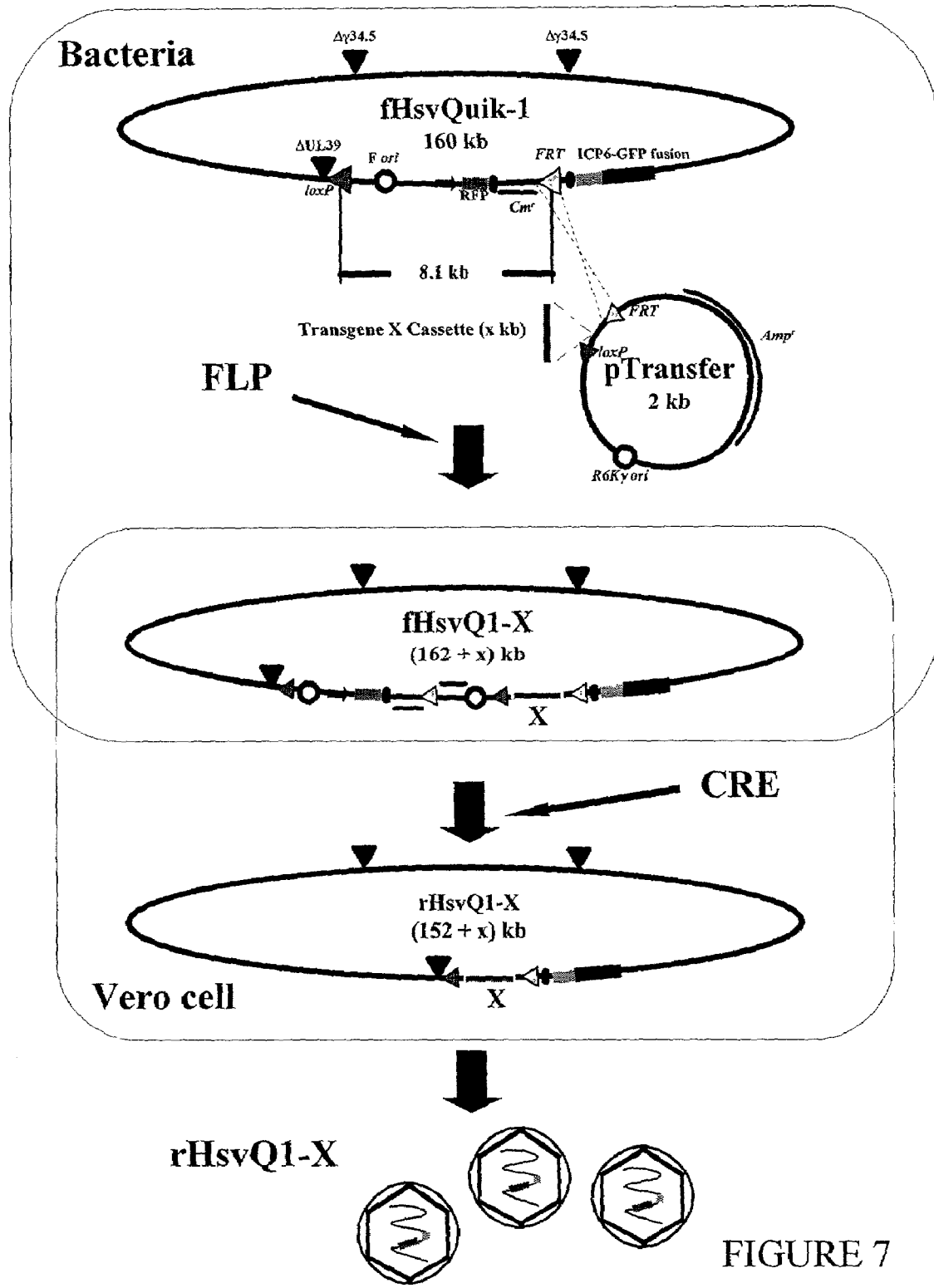

FIG. 7 is a schematic diagram of the "HsvQuik System," a rapid and efficient method to produce HSV vectors. A transgene cassette of interest (X) is cloned into the multiple cloning sites (MCS) of the replication-conditional plasmid, pTransfer. The entire sequence of the plasmid (pTransfer-X) is inserted into the fHsvQuik-1 at the FRT site by FLP-mediated recombination in E. coli. The resulting co-integrate (alternatively called "the precursor vector") is designated as fHsvQ1-X. The fHsvQ1-X construct is subsequently used to transfect VERO cells, wherein Cre-mediated recombination occurs between the loxP sites of fHsvQ1 -X, thereby removing prokaryotic backbone sequence to make the transgene-carrying HSV-1 vector rHsvQ1 -X.

Figure 8:
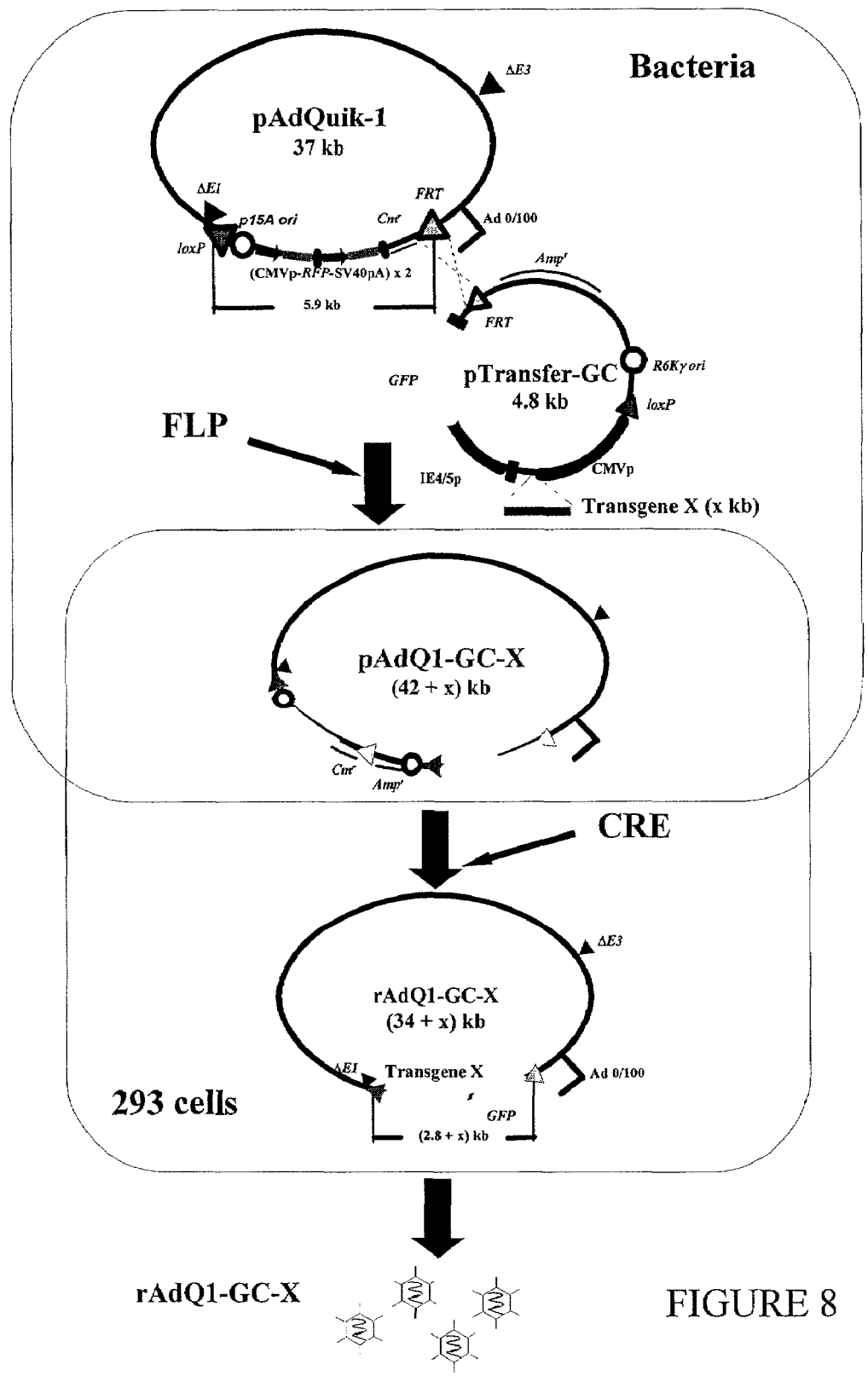

FIG. 8 is a schematic diagram of the "AdQuik System," a rapid and efficient method to produce adenoviral vectors. A transgene cassette of interest (X) is cloned into the multiple cloning sites (MCS) of the replication-conditional plasmid, pTransfer-GC. The entire sequence of the plasmid (pTransfer-GC-X) is inserted into the pAdQuik-1 at the FRT site by FLP-mediated recombination in E. coli. The resulting co-integrate (alternatively called "the precursor vector") is designated as pAdQ1-GC-X. The pAdQ1GC-X plasmid is subsequently used to transfect 293 cells wherein Cre-mediated recombination occurs between the loxP sites of pAdQ1-GC-X, thereby removing the prokaryotic backbone sequence to make the transgene-carrying Ad vector rAdQ1-GC-X.

Figure 9:
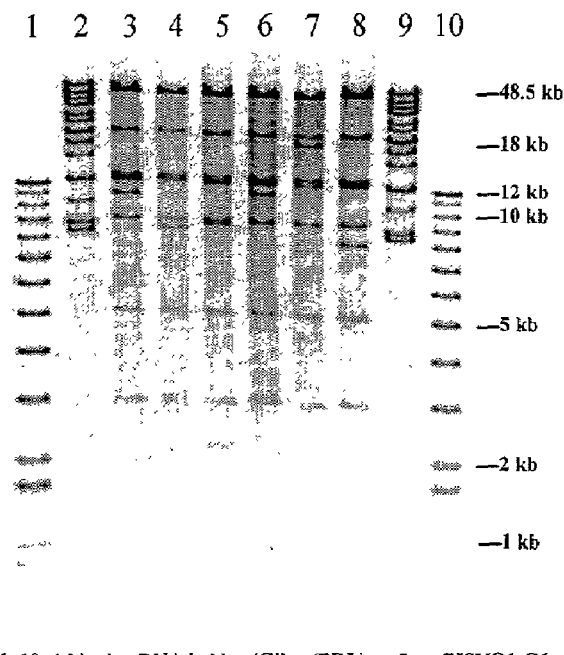
Figure 9:
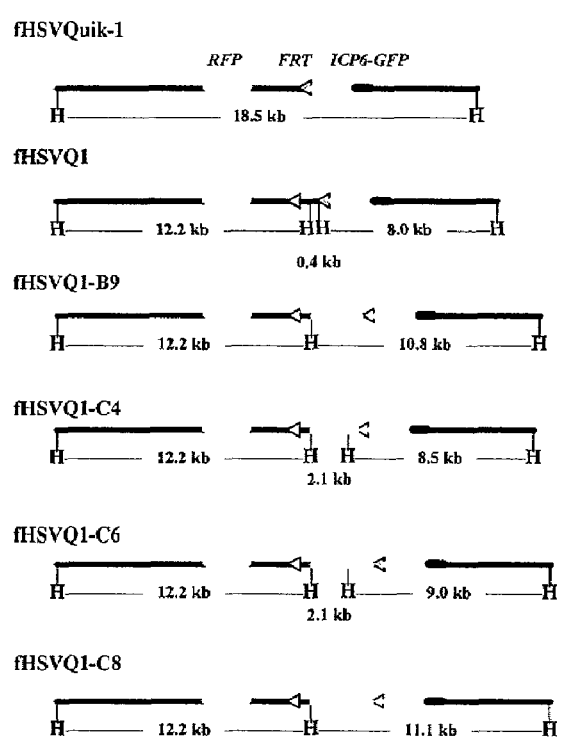

FIG. 9 depicts the restriction enzyme (HindIII) digestion analysis of HSV-BAC clones.

Figure 10:
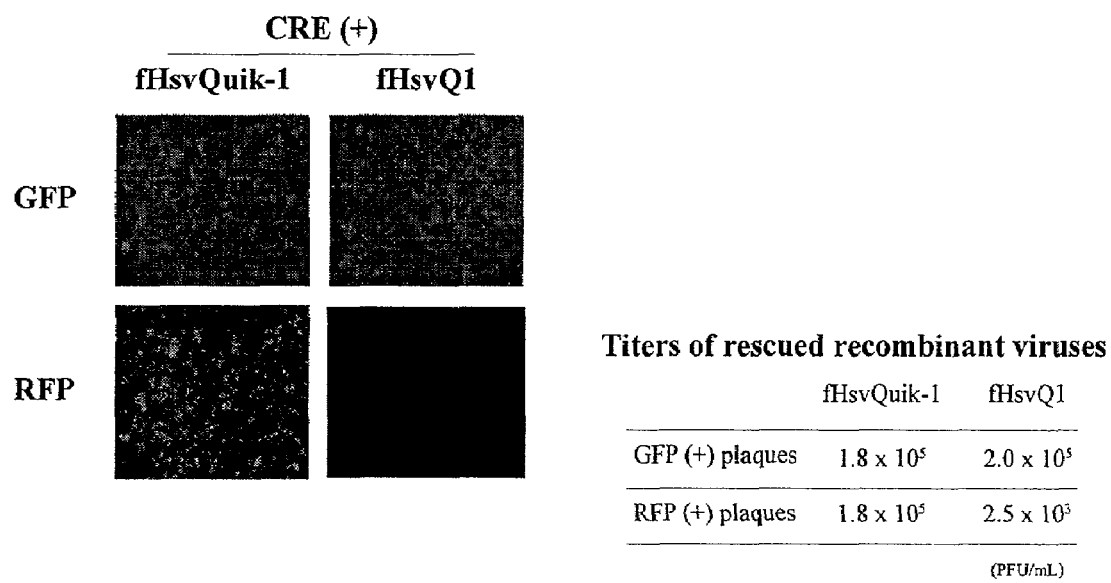

FIG. 10 depicts the successful CRE-mediated excision of the prokaryotic backbone of fHsvQ1 by the loss of red fluorescent protein (RFP) expression. VERO cells were cotransfected with pcnCRE and either fHsvQuik-1 or fHsvQ1. Sixty hours later, the progenyviruses were harvested, serially diluted, and inoculated onto VERO cells plated in 96 well-plates.

Viral plaques derived from fHsvQuik-1 showed both GFP and RFP signals, while those from fHsvQ1 showed GFP signal only. This indicates that the prokaryotic backbone of fHsvQ1 flanked by two loxP sites was successfully excised.

Figure 11:
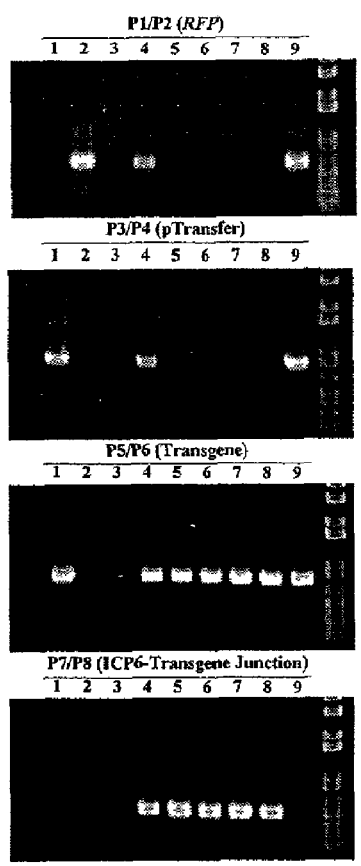
Figure 11:
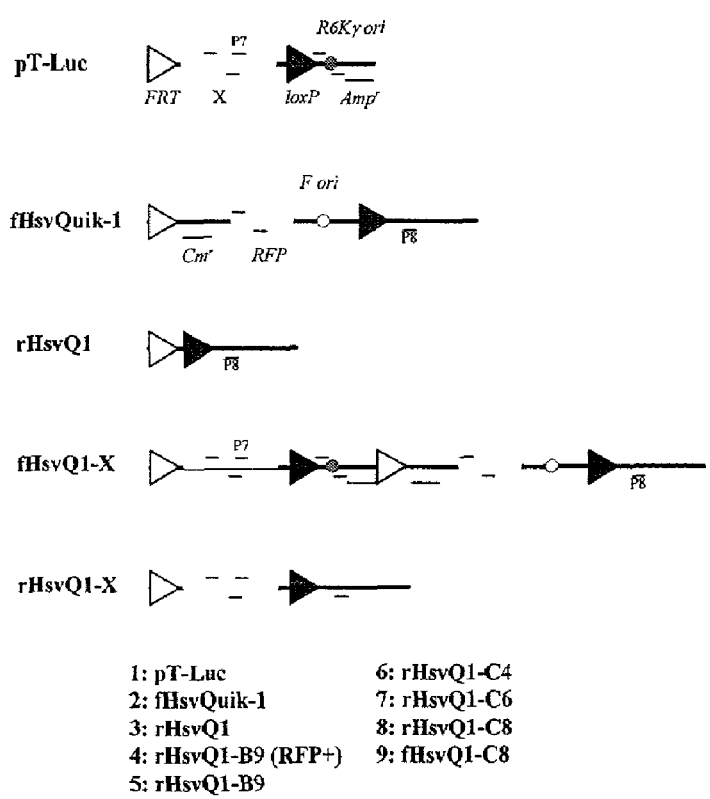

FIG. 11 depicts the PCR analysis of rescued rHsvQ1s.

Figure 12:
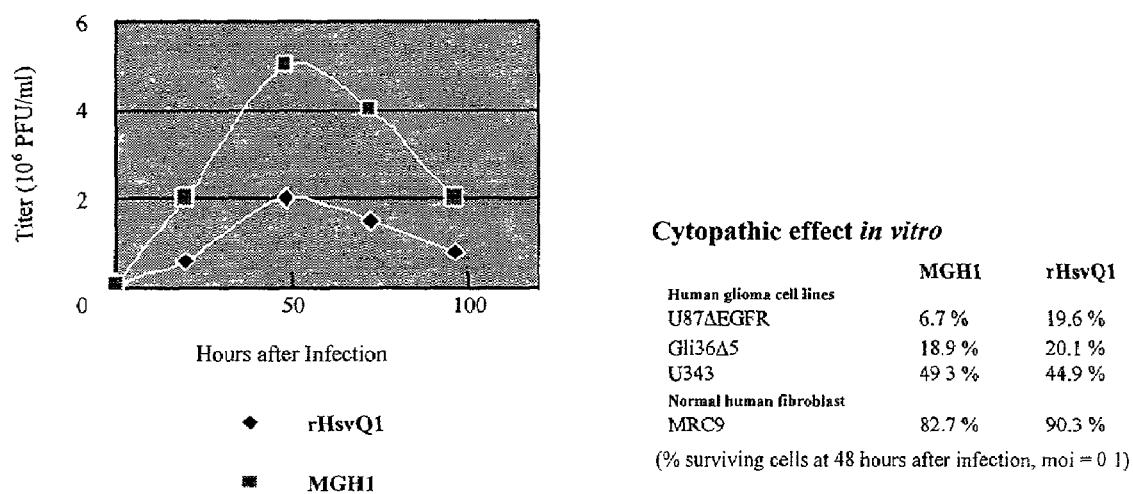

FIG. 12 depicts the characterization of rHsvQ1.

Figure 13:
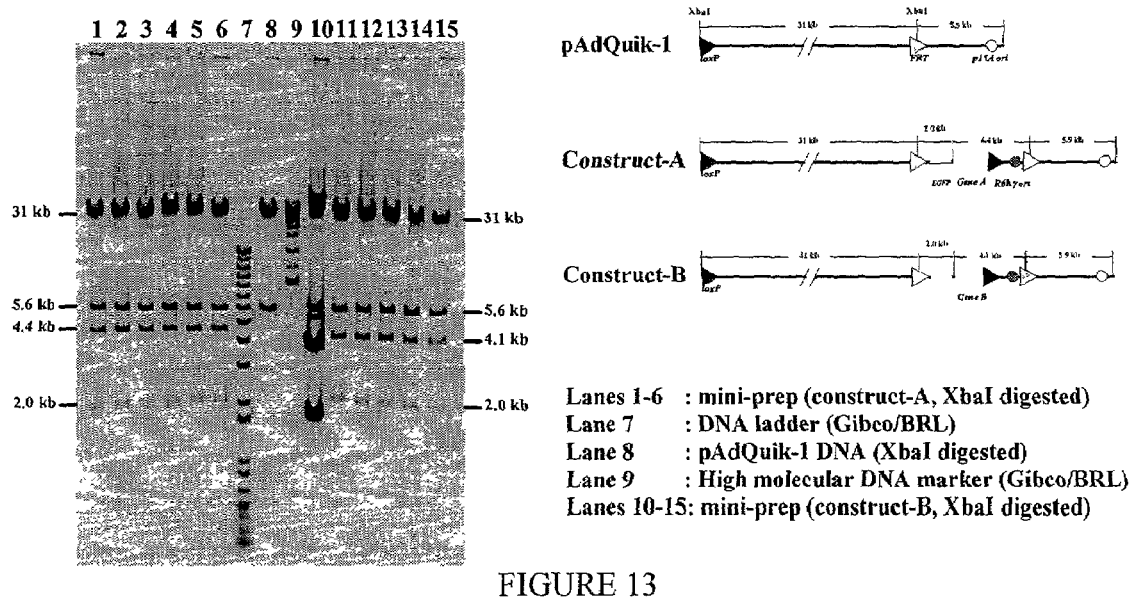

FIG. 13 depicts the restriction enzyme digestion analysis of miniprep DNA and pAdQuik-1 DNA (XbaI digested).

Figure 14:
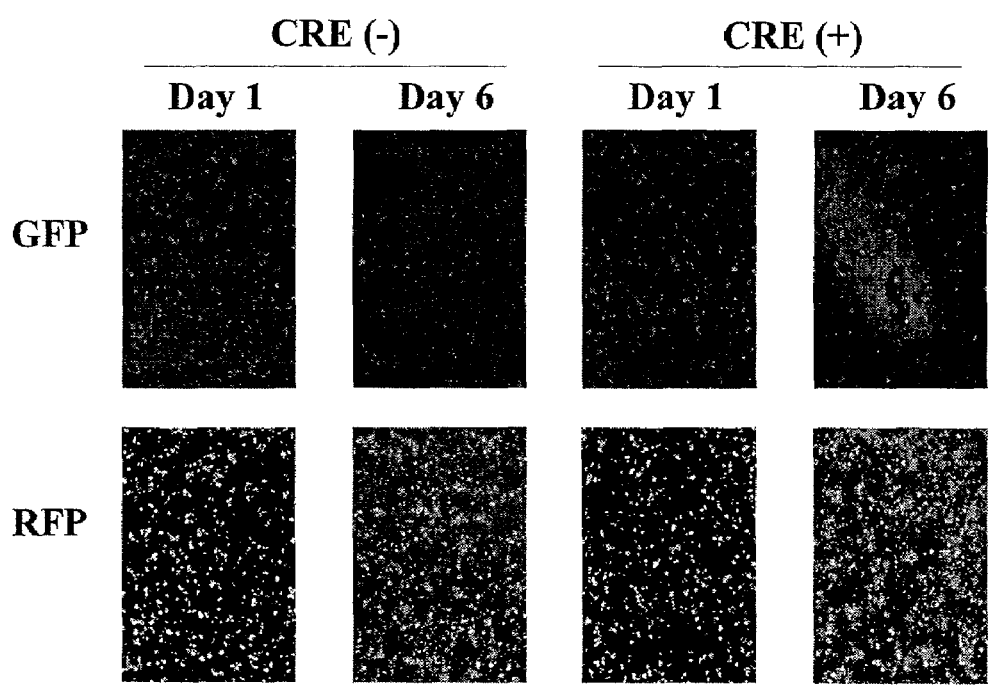

FIG. 14 depicts the CRE-mediated excision of the prokaryotic backbone in HEK293 cells. HEK 293 cells were transfected with pAdQ1-GC Luc DNA alone or pAdQ1 -GC-Luc and pcnCRE DNA using LipofectAMINE (Gibco/BRL). A number of adenovirus producing foci were detected in the culture transfected with pcnCRE.

Figure 15:
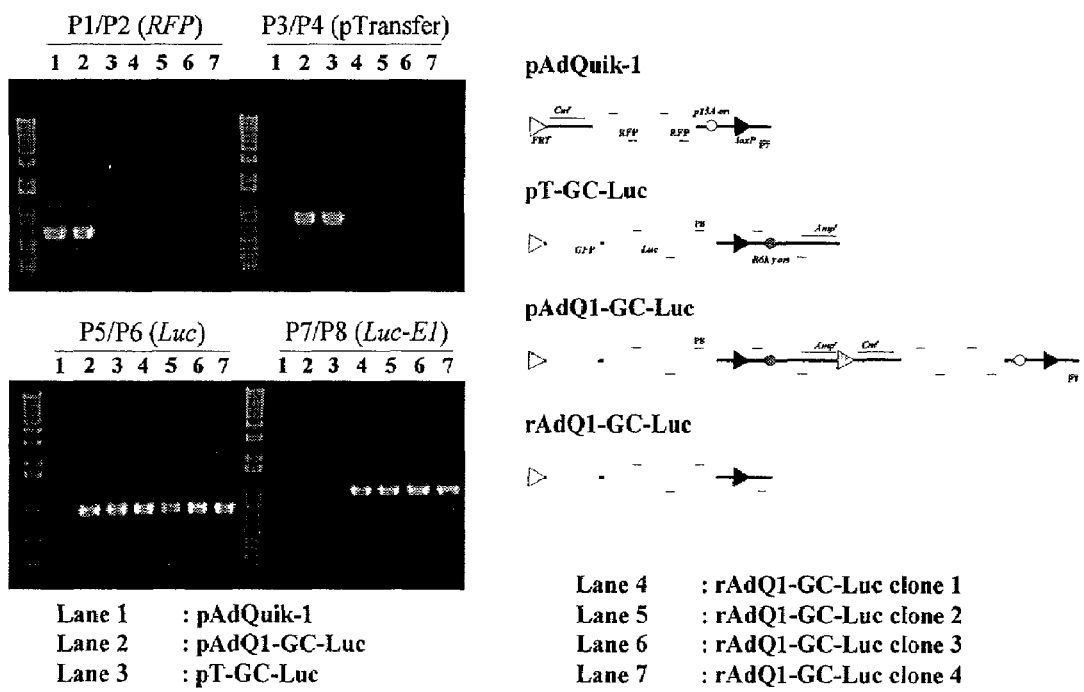

FIG. 15 depicts the PCR analysis of rescued rAdQ1-GC-Luc.

Figure 16:
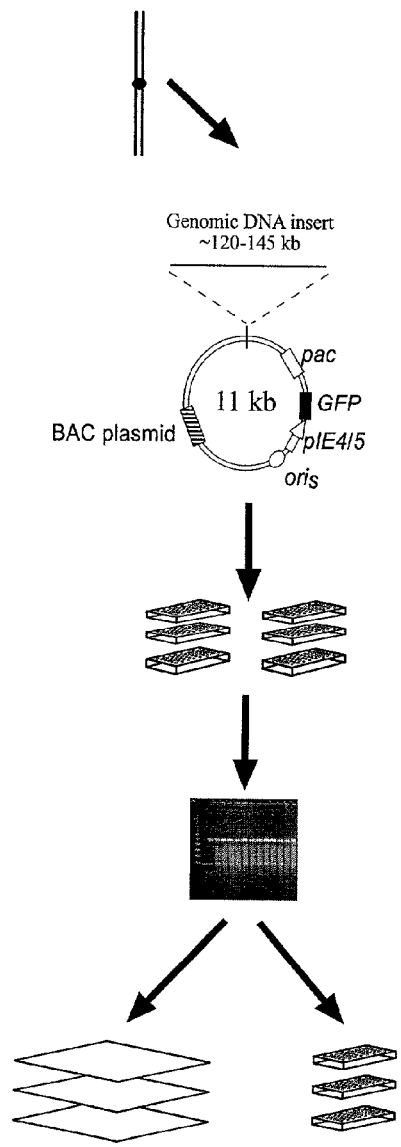

FIG. 16 depicts the construction and characterization of a pHSVBAC library. Chromosomal DNA is partially digested with BamHI and subcloned into a pHSV-BAC vector. Individual clones (approximately 200,000–500,000) are picked and the library is characterized. Platforms for library screening are then built.

Figure 17:
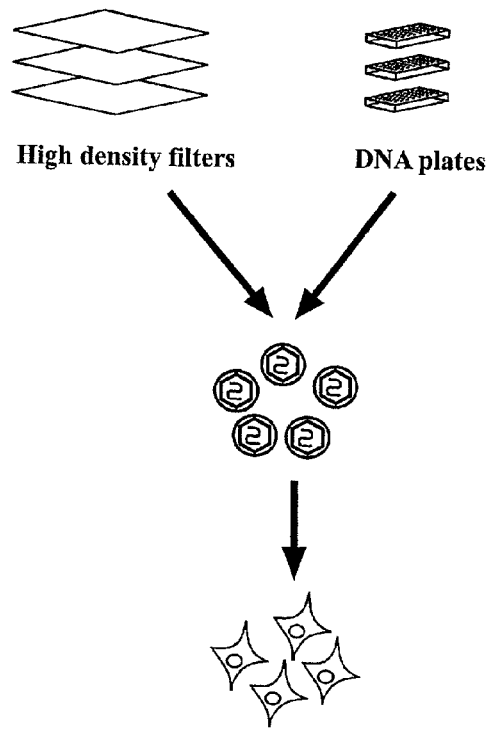

FIG. 17 depicts a method for screening a genomic DNA library to obtain clones for functional studies. The library is first screened to identify clones using either high density filters for hybridization or DNA plates of pooled DNA for PCR. The identified clones are packaged as an HSV-1 vector. Next, a cell line of interest is infected, and gene function is assayed.

Figure 18:
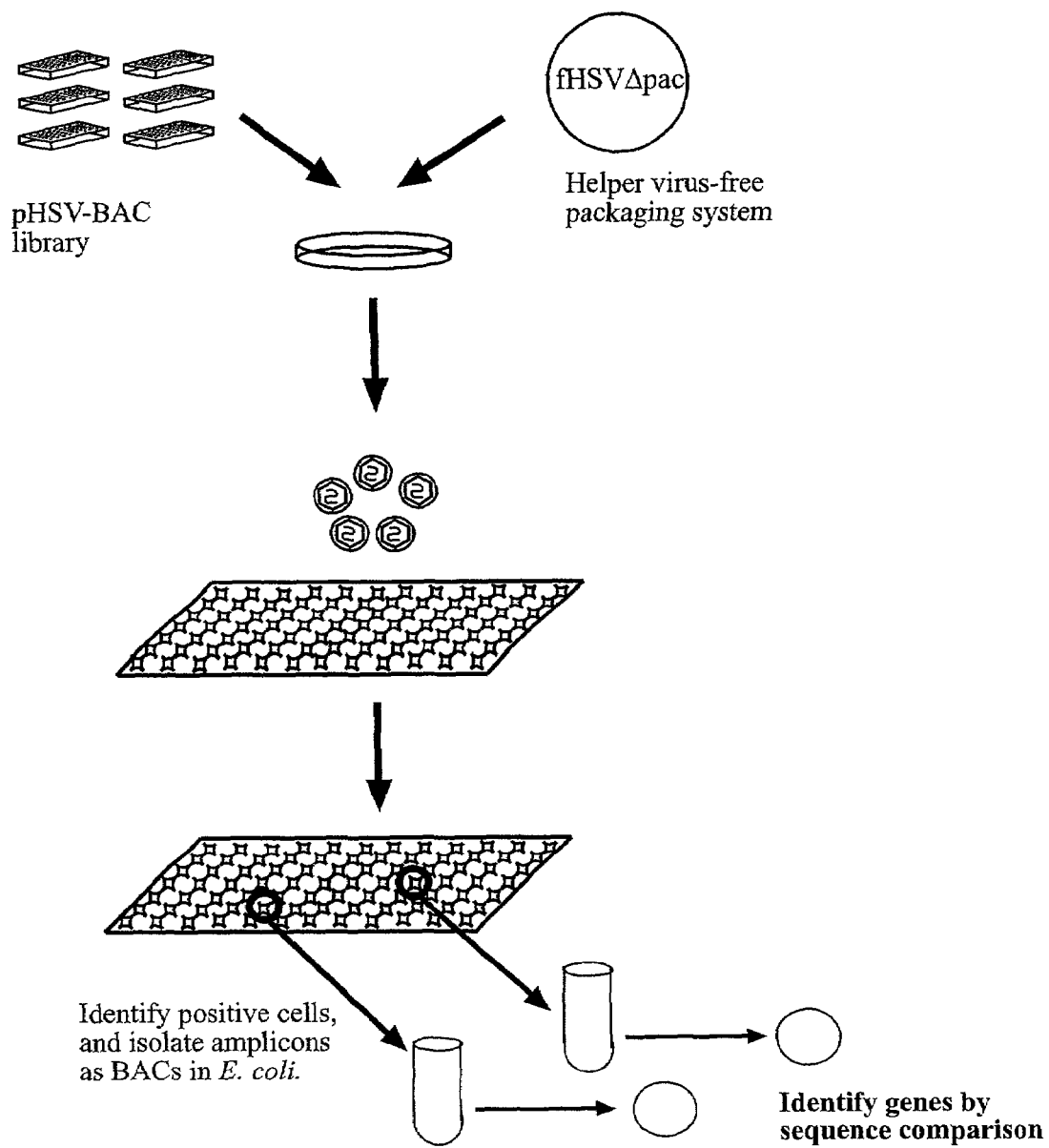

FIG. 18 depicts a method for screening a genomic DNA library by functional assay. The pHSV-BAC library is packaged into amplicon particles which are then added to a high density cell array. A functional screen on transduced cells is performed and genes are identified by sequence comparison.

DETAILED DESCRIPTION OF THE INVENTION

The present invention is directed to a herpes simplex virus (HSV)-based amplicon vector carrying a genomic DNA fragment. The invention is further directed to methods of constructing a herpes simplex virus (HSV)-based amplicon. In one aspect of the invention, an HSV-based amplicon vector carrying a genomic DNA fragment is provided comprising: (a) a large capacity cloning vector, (b) a herpes virus origin of replication, (c) a herpes virus cleavage/packaging signal, and (d) a genomic DNA fragment; wherein said HSV-based amplicon vector can infect and deliver said genomic DNA to a target cell.

In another aspect of the invention an improved and simplified method is provided for converting large capacity DNA cloning vectors, such as, e.g. a bacterial artificial chromosome (BAC) clone or a P1-artificial chromosome (PAC) clone into herpes simplex virus (HSV)-based amplicons, so that large genomic transgenes within the large capacity DNA cloning vector can be more efficiently delivered to a target cell, and expressed in vitro or in vivo.

More specifically, in an exemplified embodiment of the present invention, loxP/cre-mediated recombination was used to convert BAC or PAC clones into HSV and HSV/EBV hybrid amplicons. In this way, two large genomic DNA transgenes (containing the complete 44 kb locus of HPRT, and the complete 45 kb locus of LDLR, respectively) within the BAC or PAC were delivered by infectious transfer to target cells, and expressed, in vitro.

Since the present method involves an infectious viral system, rather than the much less efficient process of physical transfection, the present method is capable of delivering intact vector more efficiently and easily than those shown in the art.

By "infectious transfer" is intended the use of viral structural elements (such as the HSV capsid and envelop and associated proteins) to deliver into target cells a genomic region of DNA by the attachment of the viral structure to target cell receptors and then subsequent delivery of the genomic DNA into the target cell nucleus.

By "target cell" is intended any cell or cell population which the HSV-based amplicon can infect.

Thus, the present invention provides a method of converting a large capacity cloning vehicle containing genomic DNA into a herpes simplex virus (HSV)-based amplicon, such that said HSV-based amplicon can infect and deliver said genomic DNA to a cell, comprising recombining said HSV-based amplicon vector with said large capacity cloning vehicle using recombination. Although site-specific recombination is preferred, any other type of recombination known to those skilled in the art may be used as well, including homologous recombination or ligation.

The present invention also provides a method of constructing a HSV-based amplicon carrying a genomic DNA fragment comprising subcloning said genomic DNA fragment into a cloning vehicle comprising: (a) a large capacity cloning vector, (b) a herpes virus origin of replication, and (c) a herpes virus cleavage/packaging signal; such that said HSV-based amplicon can infect and deliver said genomic DNA to a target cell.

The present method utilizes a large capacity cloning vector, such as a BAC or a PAC. Although a BAC or PAC is a particularly preferred large capacity cloning vector, other large capacity cloning vectors known to those skilled in the art can also be used in the present invention. These include, e.g., cosmids (Evans et al., *Gene* 79:9–20 (1989)), yeast artificial chromosomes (YACS) (Sambrook, J., et al., *A Molecular Cloning: A Laboratory Manual*, 2$^{nd}$ Edition, Cold Spring Harbor Press, Cold Spring Harbor, N.Y. (1989), mammalian artificial chromosomes (Vos et al., *Nature Biotechnology* 15:1257–1259 (1997), human artificial chromosomes (Harrington et al., *Nature Genetics* 15: 345–354 (1997)), or viral-based vectors, such as, e.g., CMV, EBV, or baculovirus.

As used herein, the term "BAC" (Bacterial Artificial Chromosome) is intended to mean a cloning and sequencing vector derived from a bacterial chromosome into which a large genomic DNA fragment, typically up to 400 kb, can be inserted. BACs are based on the single-copy F-plasmid of *E. coli* and have been demonstrated previously to stably maintain human genomic DNA of >300 kb, and genomes of large DNA viruses, including those of baculovirus and murine cytomegalovirus (Shizuya, H., et al., *Proc. Natl. Acad. Sci. USA* 89:8794–8797 (1992); Luckow, V. A., et al., *J. Virol.* 67:4566–4579 (1993); Messerle, M., et al., *Proc. Natl. Acad. Sci. USA* 94:14759–14763 (1997)).

As used herein, the term "PAC" is intended to mean a cloning and sequencing vector derived from a P1 bacteriophage into which a large genomic DNA fragment, typically up to 300 kb can be inserted. PACs are described in Ioannou, P. A., et al., *Nature Genetics* 6:84–89 (1994) and Sternberg et al., *Proc. Natl Acad Sci USA* 87:103–107 (1990).

BAC or PAC libraries, and especially those containing human genomic DNA as a result of the Human Genome Project, are readily available to those skilled in the art (See, e.g., Simon, M. I., *Nature Biotechnol.* 15:839 (1997); http//www.ncbi.nlm.gov).

The present method also utilizes a herpes simplex virus (HSV)-based amplicon. As used herein, the term "HSV-based amplicon" includes HSV amplicons alone (HSV-1 or HSV-2), or HSV amplicons combined with genetic elements from another herpes virus, such as EBV. HSV-1 is a particularly preferred herpes simplex virus amplicon. Thus, the HSV-based amplicon that is used in the method of the invention may comprise an HSV-1 amplicon, alone, or as a component of an HSV-1 hybrid amplicon (e.g., EBV could be used together with HSV). The hybrid HSV-1/EBV amplicon is a particularly preferred herpes simplex virus-based amplicon. Other viral vector systems may be used in conjunction with the present invention, including systems based on cytomegalovirus (CMV), EBV, or baculovirus.

The vector used to transfer the amplicon elements to the large capacity cloning vector contains the herpesvirus cleavage/packaging sequence (pac) and an origin of DNA replication (ori$_s$) and flanking DNA sequences. These HSV-1 amplicon elements are recognized by the replication proteins and enzymes made by the helper packaging vector or virus. The origin of DNA replication used is preferably a herpesvirus origin of replication, and most preferably that of HSV-1. In the case of an HSV-1 hybrid amplicon, the transfer vector may also contain other viral elements, for example those of EBV in the case of a HSV-1/EBV hybrid. When the elements on the transfer vector are added to the large capacity cloning vector, the large capacity cloning vector can now be packaged as an HSV-1 amplicon, preferably by a helper virus-free system, most preferably that of Saeki et al. (Saeki, Y., et al., *Molecular Therapy* 3:591–601 (2001); International Patent Publication WO 0034497).

The method of the invention is accomplished through recombination between the large capacity cloning vector (i.e., BAC/PAC) and the HSV-based amplicon. Site-specific recombinases, such as, e.g., P1 bacteriophage CRE, yeast FLP (from *Saccharomyces cerevisiae*), yeast R recombinase (from *Zygosaccharomyces rouxii*), etc. (Sauer, B., *Curr. Opin. Biotechnol.* 5:521–527 (1994); Rossant, J., et al., *Nature Med.* 1: 592–594 (June 1995); Roder, J., et al., *Nature Genet.* 12: 6–8 (January 1996); Kilby, N. J., et al., *Trends Genet.* 9:413–421 (December 1993)) may be used in the method of the invention and are the preferred enzymes for recombination. In a very preferred embodiment, loxP/cre-mediated recombination is used.

Aside from site-specific recombination, other types of recombination may be employed as well, including homologous recombination (Yang, X. W., et al., *Nature Biotechnol.* 15:859–865 (1997); Zhang, Y., et al., *Nature Genet.* 20:123–128 (1998); Zhang, Y., et al., *Nature Biotechnol.* 18:1314–1317 (2000)), ligation (Wade-Martins, R., et al., *Nucl. Acids Res.* 27:1674–1682 (1999); Wade-Martins, R., et al., *Nature Biotechnol.* 18:1311–1314 (2000)), or any other recombination procedure known to the skilled artisan.

The method of the invention can also be accomplished by subcloning a genomic DNA fragment into a cloning vehicle that comprises (a) a large capacity cloning vector, (b) a herpes virus origin of replication, and (c) a herpes virus cleavage/packaging signal. Methods of subcloning are well known in the art. More specifically, methods of moving large DNA inserts from one large capacity cloning vector into another large capacity cloning vector have been described (Wade-Martins, R., et al., *Nucl. Acids Res.* 27:1674–1682 (1999); Wade-Martins, R., et al., *Nature Biotechnol.* 18:1311–1314 (2000)).

The genomic DNA contained within the large capacity cloning vector may be human or non-human, e.g., animal, mammalian, avian, mouse, amphibian, and the like. The genomic DNA contained within the large capacity cloning vector may be any size, preferably between 50–100 kb, and most preferably between 100–150 kb.

In one embodiment, the genomic DNA contained in the BAC or PAC may contain a gene that encodes a protein, for example, a therapeutic protein, such as, for example, one that compensates for an inherited or acquired deficiency. Examples of therapeutic proteins include neurotransmitter biosynthetic enzymes, e.g., tyrosine hydroxylase for the treatment of Parkinson's disease; neurotrophic factors including neurotrophins, e.g., nerve growth factor for the treatment of Alzheimer's disease, one can also use nerve growth factor receptor and the trk receptor; hypoxanthine-guanine phosphoribosyl transferase (HGPRT) for the treatment of Lesch Nyhan disease; β-hexosaminidase a chain for the treatment of Tay Sachs disease; insulin for the treatment of diabetes. Receptors can also be prepared, e.g. the nerve growth factor receptor, the trk receptor, and the low density lipoprotein receptor (LDLR) for the treatment of familial hypercholesterolemia (FH). Because the insert can be large, it is possible to encode a series of different proteins with large promoter elements. For example, one can encode a series of proteins that form a receptor-ligand complex under cell-specific or exogenously regulated gene expression.

Other proteins include, for example, signal transduction enzymes, e.g., protein kinase c; transcription factors, e.g., c-fos, NF-Kβ; oncogenes, e.g., erbB, erbB-2/neu, ras; neurotransmitter receptors, e.g., glutamate receptor, dopamine receptor; heat shock proteins; anti-apoptotic factors; anti-oncogenic proteins; prodrug activating enzymes; immune enhancers; imaging proteins; and angiogenic or anti-angiogenic factors. In addition, normal genes can be carried for gene correction or supplementation of normal gene products. The nucleotide sequence can also encode specific antigenic peptide sequences that will generate an immunogenic reaction.

Specific knowledge of a gene's presence or function, however, is not necessary in this method, as functional genomic assays can be performed to determine the presence or function of a gene in a particular genomic insert.

Alternatively, in another embodiment, the genomic DNA may contain regulatory or controlling DNA sequences, including promoter regions, and thus may not code for a protein.

Also, the genomic DNA may comprise human or mammalian centromeric DNA for the creation of human or mammalian artificial chromosomes.

In a particular embodiment described below in Example 1, a simple method for converting any BAC or PAC library clone into an HSV-1/EBV hybrid amplicon is presented. This Example demonstrates for the first time that HSV-1 amplicon vectors can deliver BAC and PAC genomic DNA inserts of over 100 kb. The amplicons were packaged into virions by a HSV-1 helper virus-free packaging system (Saeki, Y., et al., *Molecular Therapy* (2001), supra, International Patent Publication WO 00/34497), and were able to recircularize following infection.

The vector system described has a number of advantages. It combines the ease of manipulation of the BAC and PAC cloning systems, the efficiency and large transgene capacity of HSV-1 amplicon gene delivery, and the extrachromosomal maintenance mechanism of EBV-based episomes. As such, it represents a potentially powerful new technology for functional genomics and gene therapy. HSV-1 amplicons are an excellent platform for the delivery of BAC and PAC inserts because: (i) HSV-1 has a high transgene capacity of approximately 150 kb; (ii) high-titre amplicon stocks can be produced by helper virus-free packaging systems; and (iii) the resulting virion particles have a broad cell tropism across a wide range of species. It is believed that HSV-1 is unique in being able to combine all these features. Other large insert systems (such as EBV or CMV) are not able to combine all of the features that HSV-1 can.

The herpesvirus amplicon of the present invention can be used to deliver heterologous DNA to a target cell. The target cell may be in vivo, ex vivo, or in culture. Mammalian target cells are preferred. The target cell can be a dividing or quiescent cell. Quiescent cells include postmitotic cells. The preferred postmitotic cells are glia, neurons, hepatocytes, muscle cells, macrophages, etc.

Introduction of the viral particle carrying the heterologous gene to be delivered to the target cell may be effected by any method known to those of skill in the art. For example, stereotaxic injection can be used to direct the viral particles to desired locations in the brain. Stereotaxic surgery is performed using standard neurosurgical procedures (Pellegrino, L. J. and Cushman, A. J., "*Methods in Psychobiology,*" Academic Press, New York, N.Y., pp. 67–90 (1971)). Additionally, the particles can be delivered by intracerebroventricular ("icv") infusion using a minipump infusion system, such as a SynchroMed Infusion System. A recent method based on bulk flow, termed convection, has also proven effective at delivering large molecules to extended areas of the brain and may be useful in delivering the viral particle to the target cell (Bobo, R. H., et al., *Proc. Natl. Acad. Sci.* 91:2076–2080 (1994); Morrison, P. F., et al., *Am. J Physiol.* 266:292–305 (1994)). Other methods can be used including catheters, intravenous, parenteral, intraperitoneal and subcutaneous injection, oral or other known routes of administration.

One would inject a sufficient amount of the viral particles to obtain a serum concentration in the tissue containing the target cell of the therapeutic protein ranging between about 1 µg/ml to 20 µg/ml. More preferably between about 0.1 µg/ml to 10 µg/ml. Still more preferably, between about 0.5 µg/ml to 10 µg/ml.

For example, solid dose forms that can be used for oral administration include capsules, tablets, pills, powders, liposome emulsions, and granules. In such solid dose forms, the active ingredient, i.e., empty virus particle, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the virus particle. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml, more preferably, about 3 mg/ml to about 10 mg/ml.

In another aspect of the invention, a system is provided that allows for the rapid and efficient creation of viral vectors, e.g., herpes simplex virus (HSV) vectors or adenovirus (Ad) vectors, carrying transgenes of interest.

In an exemplary embodiment of this aspect of the invention, two components are provided. The first component (component 1) is a large capacity cloning vector or plasmid carrying a viral genome. The large capacity cloning vector may be a BAC or PAC or any other suitable vector or plasmid known by persons skilled in the art. Preferably, the vector or plasmid backbone sequence is flanked by two non-identical site-specific recombinase recognition sequences; e.g., loxP (recognized by the Cre recombinase) and FRT (recognized by the Flp recombinase). Any recombination system may be used in the present invention. Additionally, the first component may also carry a marker gene such as green fluorescent protein (GFP) or enhanced green fluorescent protein (EGFP), which can be used to identify infected cells.

The second component (component 2) is a transfer vector carrying a transgene of interest. The transfer vector backbone can be any suitable vector known by persons skilled in the art. In a preferred embodiment, the transfer vector also carries a conditional origin of replication. Preferably, the transgene of component 2 is flanked by two different site specific recombinase recognition sequences corresponding to those found in component 1.

According to this aspect of the invention, a viral vector carrying a transgene of interest can be created by first co-transforming an appropriate bacterial cell (E. coli, for example) with the viral genome-carrying vector or plasmid (component 1) and the transfer vector (component 2). Through enzyme-mediated site-specific recombination (or any other recombination technique known to those skilled in the art), a precursor construct is created from the two components. In a preferred embodiment, the site-specific recombination event occurs between the FRT sites of components 1 and 2 via Flp recombinase. The bacterial cells harboring the precursor can be stored and maintained as a bacterial stock for further modification.

Next, according to this aspect of the invention, the precursor plasmid is isolated from the bacterial cell and then transfected into a host cell. The host cell can be a VERO cell, a 293 cell, or any other appropriate host cell known by those skilled in the art. Following transfection, the prokaryotic backbone or other unwanted DNA sequence may be removed from the precursor through enzyme-mediated site-specific recombination (or any other recombination technique known to those skilled in the art). In a preferred embodiment, the site specific recombination event is Cre-mediated recombination that occurs between the loxP sites found on the precursor, thereby creating a viral vector carrying the transgene of interest. Virus particles containing the resultant vector can then be obtained from the host cell.

In another aspect of the invention, an expression-ready genomic DNA library is provided for use in functional genomics.

In an exemplary embodiment of this aspect of the invention, the library is comprised of a plurality of vectors, each vector comprising: (a) a large capacity cloning vector, (b) a herpes virus origin of replication, (c) a herpes virus cleavage/packaging signal, and (d) a genomic DNA fragment. The large capacity cloning vector can be a BAC or PAC or any other suitable vector or plasmid known by persons skilled in the art. The herpes virus origin of replication, and the herpes virus cleavage/packaging signal, can be derived from HSV-1.

According to this aspect of the invention, the vectors of the library are capable of being propagated within bacterial cells and are also capable of being packaged into infectious particles. The vectors can be packaged into infectious particles by any method known by those skilled in the art. In one embodiment, the vectors are packaged using a helper virus free packaging system.

The genomic DNA fragment of this aspect of the invention can be derived from any species of interest, including human, mouse and rat.

In another aspect of the invention, a method is provided for isolating a genomic DNA clone encoding a gene product with a preselected function.

According to this aspect of the invention, an infectious, expression-ready genomic DNA library is obtained. The library is comprised of a plurality of vectors, each vector comprising: (a) a large capacity cloning vector, (b) a herpes virus origin of replication, (c) a herpes virus cleavage/packaging signal, and (d) a genomic DNA fragment.

According to this aspect of the invention, the vectors of the library are packaged into infectious particles. The vectors can be packaged into infectious particles by any method known by those skilled in the art. In one embodiment, the vectors are packaged using a helper virus free packaging system.

The infectious particles packaged according to this aspect of the invention are then used to infect model cells. Model cells can be any cells that permit the identification of the preselected function. Exemplary model cells include human or mouse cells or primary cells. Individual infected cells are identified that exhibit a phenotype indicative of the preselected function, and the genomic DNA fragment of the library vector is isolated. The nucleotide sequence of the isolated genomic DNA fragment can then be determined.

The present invention is further illustrated by the following Examples. These Examples are provided to aid in the understanding of the invention and are not to be construed as a limitation thereof.

EXAMPLES

Example 1

Transfer of Large Functional Transgenes by Infectious Delivery

In this Example, a hybrid technology is presented based on the fusion of an HSV-1/EBV amplicon vector and the BAC/PAC cloning systems. The resulting high capacity amplicon fully exploits the ~150 kb capacity of HSV1. Using this system, BAC or PAC inserts of >100 kb can be delivered by infectious transfer. The utility of the system was demonstrated by the transfer of two different large functional genomic DNA transgenes by infectious delivery.

First, functional delivery of the complete 44 kb locus of the human hypoxanthine phosphoribosyltransferase (HPRT) gene contained within a 115 kb genomic DNA BAC insert was shown. HPRT is a housekeeping enzyme expressed in all cells and catalyses an early step in the purine salvage pathway in mammalian cells. The human HPRT locus lies at Xq26.1 and mutations within the gene cause the debilitating diseases of Lesch-Nyhan syndrome and gouty arthritis (Caskey, C. T., and Kruh, G. D., *Cell* 16:1–9 (1979); Davidson, B. L., et al., *Am. J. Hum. Genet.* 48:951–958 (1991)). The human fibroblast HPRT-deficient cell line used in this study exhibits a complete lack of HPRT enzymatic activity. When the HPRT genomic DNA transgene was delivered using the HSV-1/EBV hybrid system, the gene was functional both in a transient infection assay and in selected clonal cell lines in which the transgene was maintained as an episome. It is expected that the genomic DNA transgene will be functional in vivo following infectious transfer to the brain of hprt-deficient mice (Hooper, M., et al., *Nature* 326:292–295 (1987)). The vector system has considerable potential for the delivery of large genomic transgenes in functional genomics and gene therapy applications.

Second, the complete 45 kb genomic locus of the low density lipoprotein receptor (LDLR) was delivered within a 135 kb genomic DNA BAC insert to the ldlr deficient strain of Chinese hamster ovary cells (CHO ldlr-/- a7) in vitro. The LDLR gene is mutated in the human disease familial hypercholesterolemia (FH). The LDLR protein controls LDL levels in the blood, and a lack of the receptor results in high circulating levels of cholesterol, leading to atherosclerosis. FH is fatal and incurable, so expression systems for LDLR have important therapeutic applications through gene therapy treatments.

MATERIALS AND METHODS

HPRT vector construction: The vector pEHHG contains the EBV episome retention cassette (oriP/EBNA-1/hyg$^r$) from pH300 (Wang, S., et al., *Gene Ther.* 4:1132–1141 (1997)), ori$_s$ and pac elements from pHSV-GFP (Aboody-Guterman, K. S., et al., *NeuroReport* 8:3801–3808 (1997)), and the R6Kγ bacterial replication origin. pCTP-T is described elsewhere (Saeki, Y., et al., *Molecular Therapy* (2001), supra). Six BAC and PAC constructs were converted into HSV-1/EBV amplicons using the cre-recombinase mediated system. pHSV-100 derives from PAC 63H04; pHSV-120 derives from PAC 85M20; pHSV-135 derives from PAC 298O01; pHSV-143 derives from p5255 and carries a 115 kb insert from PAC 71G04 that includes the entire HPRT gene; pHSV-153 carries a 120 kb insert from BAC 255A7; and pHSV-176 derives from BAC bWX187.

Tissue culture: MRC-5V2 (an SV40-immortalized human male lung fibroblast cell line (Huschtscha, L. I., and Holliday, R., *J Cell. Sci.* 63:77–99 (1983)) and HP10, a derivative containing a deletion of the HPRT locus on Xq26.1 (G. Dorado and A. R. Lehmann, personal communication) were cultured at 37° C. in 5% (v/v) $CO_2$ in Dulbecco's modified Eagle's medium supplemented with 10% fetal bovine serum (FBS), penicillin (100 U/ml) and streptomycin (100 µg/ml) (P/S). HP10E (HP10 cells carrying the EBNA-1 expressing helper plasmid pGEBNA (Wade-Martins, R., et al., *Nature Biotech* 18:1311–1314 (December 2000)) and 2-2 cells (a derivative of the VERO African green monkey kidney cell, which constitutively express the HSV-1 ICP27 protein) (Smith, I. L., et al., *Virology* 186:74–86 (1992)) were grown in DMEM, 10% FBS, P/S, and G418 (Geneticin) at 500 µg/ml.

HSV-1 amplicon production and infection: HSV-1 amplicons were produced using an improved HSV-1 helper virus-free system (Saeki, Y., et al, *Molecular Therapy* (2001), supra; international Patent Publication WO 0034497). For amplicon packaging, $7.5 \times 10^5$ ICP27-expressing 2-2 cells were plated in a 6 cm dish. Twenty-four hours later, the cells were cotransfected with 1.8 µg amplicon DNA, 0.2 µg pEBHICP27 (a plasmid expressing ICP27) and 2µg f-HSV Δpac Δ27 ICP0$^+$ using LipofectAMINE Plus transfection reagent (GIBCO-BRL). Sixty hours later, the cells were scraped into the supernatant, frozen and thawed once, sonicated for 20 seconds, centrifuged at 3,500 rpm for 15 minutes to remove cellular debris and, finally, the amplicon was concentrated through a 25% sucrose gradient by ultracentrifugation at 22,000 rpm in a SW 41 rotor (Beckman). The amplicon pellet was resuspended overnight in Hank's Buffered Salt Solution (HBSS). Typically, the supernatant from three 6 cm dishes was concentrated and resuspended in 200 µl HBSS giving a stock of $10^6$ transducing units/ml when titered for GFP expression on a 293 cell layer. For amplicon infection, $5 \times 10^4$ MRC-5V2 or HP10 cells were plated per well of a 24 well dish. Twenty-four hours later, the cells were infected with an HSV-1 amplicon for approximately 10–12 hours. Gardella gel electrophoresis was performed as previously described (Gardella, T., et al., *J. Virol.* 50:248–254 (1984)).

Southern blotting of amplicon DNA: For DNA analysis, amplicons were harvested by three freeze/thaw cycles instead of sonnication, and concentrated on a sucrose gradient as described. Following titration, the resuspended amplicon was incubated at 37° C. with RNaseA and DNaseI for three hours, and then with SDS/proteinase K overnight. The samples were extracted against phenol/chloroform and against chloroform, precipitated and resuspended in TE.

DNA from approximately $10^5$ viral particles was loaded per lane, resolved by pulsed field gel electrophoresis (PFGE), blotted onto nylon membrane and hybridized.

Plasmid rescue assay: Genomic DNA was prepared from cultured cells and resuspended in 20 µl TE (from a single well of a 24 well plate) or 200 µl TE (from a 10 cm dish) and 2 µl was electroporated into DH-10B ElectroMax *E. coli* cells (Gibco BRL). The transformations were then plated onto LB agar containing the appropriate antibiotics (carbenicillin [50 µg/ml], and chloramphenicol [15 µg/ml] or kanamycin [25 µg/ml]). Plasmid DNA was prepared from the resulting bacterial colonies, digested with Not I and analyzed by PFGE.

HPRT activity assay: Enzymatic activity of HPRT was measured by fluorography in non-denaturing polyacrylamide gels as previously described (Yee, J. K., et al., *Gene* 53:97–104 (1987)).

Copy number assessment: Five micrograms of genomic DNA were digested with Not I, resolved by gel electrophoresis, blotted onto nylon membrane, and hybridized with a probe specific to the GFP open reading frame. Copy numbers were obtained by comparing signal intensities (determined using a BioRad PhosphorImager) to those given by eight three-fold serial dilutions of known amounts (10–0.005 ng) of pHSV-HPRT DNA digested with Not I and mixed with 5 µg of Not I digested human DNA. One copy of a 143 kb double-stranded plasmid is approximately equivalent to 82 pg of plasmid DNA in 5 µg genomic DNA prepared from the hyperploid HP10 (modal chromosome number of 60–80 per metaphase spread).

In vivo gene delivery: Gene expression from pHSV-HPRT in vivo is being studied in the brains of the hprt-/- mouse strain B6.129P2-Hprt$^{b-m3}$. Ten microliters of pHSV-HPRT amplicon at $10^6$ tu/ml will be injected into one hemisphere of a mouse brain, with 10 µl of saline solution injected into the other hemisphere as a negative control. Expression of the reporter gene, green fluorescent protein (GFP), will be determined by direct detection of fluorescence and by antibody staining and HPRT expression will be assayed in brain slices using a [$^3$H]-hypoxanthine incorporation assay.

LDLR vector construction and delivery: The human BAC library clone 164O19 was retrofitted with the vectors pEHHG and pHG (a vector similar to pEHHG, but lacking the EBV replicon elements) as described above. Amplicon stocks of pHSV-LDLR and pHSV/EBV-LDLR were prepared as described, and used for infection into MRC-5V2 cells as described. Plasmid rescue was also performed as described.

LDLR expression assay: CHO ldlr-/- a7 cells expressing the Herpes virus entry protein C (HveC) were seeded at a density of $5 \times 10^4$ cells per well of a 24-well plate in Ham's F12 nutrient mixture containing 5% lipoprotein deficient serum (LPDS) in place of FBS. Sixteen hours later, the cells were infected with pHSV-LDLR amplicon for 10–12 hours. After the infection, the infection mixture was removed and replaced with fresh medium containing 5% LPDS. Seventy-two hours later, the cells were incubated with DiI-LDL (10 mg/ml) for five hours, and then examined for GFP expression, and for DiI fluorescence.

RESULTS

Vector Construction and Amplicon Production

In order to rapidly perform functional analyses of genomic DNA sequences in BAC and PAC libraries, a general strategy was devised in which any BAC or PAC clone from a library or database may be modified by adding sequences that will permit its packaging into an infectious amplicon vector (FIG. 1A). A model cell culture system can then be infected with the amplicon for analysis of gene expression. The retrofitting vector pEHHG (a plasmid containing EBV and HSV-1 amplicon elements, hygromycin resistance and GFP) is shown in FIG. 1B. pEHHG contains a single loxP site, which is also present in BAC and PAC vectors used in library construction (Shizuya, H., et al., *Proc. Natl. Acad. Sci. USA* 89:8794–8797 (1992); Ioannou, P. A., et al., *Nature Genet.* 6:84–89 (1994)). Cre recombinase-mediated recombination was used to retrofit a series of BAC and PAC constructs to create a size series of BAC and PAC HSV-1/EBV amplicons in the size range of 100–176 kb (FIG. 1B). The cre recombinase-mediated recombination relies upon two features: (i) pEHHG contains the R6Kγ bacterial replication origin which can only replicate in the presence of the pir protein; and (ii) the pir protein is supplied in trans by a helper plasmid pCTP-T (Saeki, Y., et al., *Molecular Therapy* (2001), supra). pCTP-T expresses pir under the control of the tetracyclin response element and replicates from a temperature sensitive (ts) replication origin which functions at 30° C., but not at 42° C.

Briefly, electro-competent DH10B *E. coli* cells were prepared carrying each parental BAC or PAC clone. Each *E. coli* line was electroporated with 10 ng of pEHHG and 10 ng of pCTP-T and incubated for 1 hour at 30° C. in SOC medium containing 20 µg/ml heat-inactivated chlortetracycline (cTc). Each bacteria culture was then diluted 1:10 into LB containing 20 µg/ml cTc and the appropriate antibiotics (carbenicillin (50 µg/ml) and chloramphenicol (15 µg/ml) [for BACs] or kanamycin (25 µg/ml) [for PACs]) and incubated at 30° C. for 3 hours. Finally, the culture was plated onto LB agar containing carbenicillin and chloramphenicol or kanamycin and incubated overnight at 42° C. Pulsed-field gel electrophoresis (PFGE) was used to identify recombinant clones which contained only a single copy of the retrofitting pEHHG cassette. Each of the six constructs shown in FIG. 1B was purified by double CsCl banding and packaged into HSV-1 virions using an improved helper virus-free system (Saeki, Y., et al., *Molecular Therapy* (2001), supra; International Patent Publication WO 00/34497). Amplicon stocks were titred by assaying GFP expression on a 293 confluent cell layer. Typically, yields of $10^6$ transducing units/ml were obtained in concentrated stocks. Undigested DNA prepared from the packaged amplicons will be analyzed by PFGE. Preliminary results suggest that we will see a size series of virion DNA.

Amplicon Infection and Recircularization

The six amplicons in the size series were used to infect the SV40-immortalized human male lung fibroblast cell line MRC-5V2 at an MOI of 1, based on the titres calculated on 293 cells. The MRC-5V2 cells were efficiently infected, with upwards of 90% of cells transduced, as assayed by GFP expression (not shown).

Two assays were performed to assess the ability of the infectious HSV-1 virion particles to deliver intact DNA to MRC-5V2 fibroblast cells by infection. First, the recircularization of amplicon DNA following infection was assayed by Gardella gel electrophoresis, a technique which allows resolution of circular episomal DNA from linear and chromosomal DNA. Circular, supercoiled DNA was seen in transduced cells forty-eight hours after infection with the HSV-1 amplicons up to 153 kb in size (not shown). No supercoiled DNA was seen following infection with pHSV-176 (not shown).

Second, genomic DNA was prepared from transduced MRC-5V2 cells forty-eight post-infection. A plasmid rescue assay was performed to assess the efficiency with which the amplicons delivered the BAC or PAC insert intact (FIG. 1C). All of the amplicons in the size range 100–153 kb were delivered intact with an efficiency of 25%–100%. This is the size range in which most BAC and PAC clones isolated from libraries falls, giving the vector system broad applicability to current PAC and BAC libraries.

Infectious Delivery of a Functional 115 kb Genomic DNA Insert

The HSV-1/EBV hybrid vector pHSV-143 (also called PHSV-HPRT) carries the complete genomic locus of the human hypoxanthine phosphoribosyltransferase (HPRT) gene within a 115 kb genomic DNA insert. The ability of the vector system to deliver an intact functional genomic DNA transgene was tested by assaying HPRT expression from pHSV-HPRT in two contexts: first, in transient expression assays, and second, in stable clonal cell lines.

Initially, pHSV-HPRT amplicon DNA was analyzed undigested by pulsed field gel electrophoresis followed by Southern blotting and hybridization (FIG. 2A). A linear band of approximately 143 kb was seen, consistent with the expected size of a monomer of pHSV-HPRT. The pHSVH-PRT amplicon was then used to infect HP10 cells, an HPRT-deficient strain of the MRC-5V2 human fibroblast cell line. At an MOI of 1, the HP10 cells were transduced by pHSV-HPRT with an efficiency of approximately 70%, based on GFP expression (not shown). In the first assay, transduced cells grown in the absence of selection were harvested at several time-points postinfection and HPRT expression was assayed by a gel activity assay (FIG. 2B). HPRT activity can be clearly seen at all time-points, with strongest activity seven days post-infection. Quantitation of expression by PhosphorImager analysis of the signal intensities on the activity gel showed HPRT expression from HP10 cells infected with pHSV-HPRT to be 47% of MRC-5V2 activity at seven days post-infection. As a control to demonstrate that expression is brought about by infectious delivery of the HPRT locus, a control amplicon lacking the pac signal (pHSV-HPRTΔpac) was prepared in an identical manner, and was used to infect HP10 cells with an approximately equivalent number of empty viral particles. No activity was seen following transduction with pHSV-HPRTΔpac, consistent with the infectious transfer of HPRT activity by pHSV-HPRT. No activity was seen in HP10 cells infected with pEHHG and infection with pEHHG was also seen not to affect HPRT expression in wild-type MRC-5V2 cells. A second expression assay was used to confirm HPRT activity at the level of individual cells. Seventy-two hours post-infection with pHSV-HPRT HP10 cells were incubated in medium containing [$^3$H]-hypoxanthine and HPRT expression was assayed by autoradiography (FIG. 2C). A high proportion of cells showing GFP expression were also positive for HPRT activity (FIG. 2C, lower two panels), confirming the high efficiency of infectious delivery of the functional genomic DNA transgene.

Infectious Delivery of pHSV-HPRT to Mouse Primary Hepatocyte Cultures

Primary cell lines established from mouse models of human disease are a valuable resource for studying transgene expression. However, such cells are often resistant to transfection. Viral delivery of genomic DNA transgenes has the potential to overcome the reduced efficiency associated with transfection of large (>100 kb) DNA constructs. We compared the relative efficiency of delivery of pHSV-HPRT (143 kb) by parallel pHSV-HPRT amplicon infection and pHSV-HPRT plasmid transfection using three commercially available reagents on primary hepatocyte cultures derived from two mouse strains (FIG. 3A). GFP expression showed infectious delivery to be many times more efficient than transfection with the three reagents tested. Control parallel transfection of 293 cells showed good transfection levels of 5–10% as expected for this size plasmid, and as high as 30–40% for LipofectAMINE Plus (not shown). Infection and autoradiography of hepatocytes derived from B6.129P2-Hprt$^{b-m3}$ mice (Hooper, M., et al., Nature 326:292–295 (1987)) confirmed that the pHSV-HPRT genomic transgene is functional in mouse primary hepatocytes following transduction (FIG. 3B).

Long-Term Episomal Vector Retention and Gene Expression

For long-term expression assays, pHSV-HPRT was used to infect HP10 and HP10E (an HP10 EBNA-1$^+$ cell line carrying the helper plasmid pGEBNA (Wade-Martins, R., et al., Nature Biotech 18:1311–1314 (December 2000)) at an MOI of 0.2. Forty-eight hours post-infection, the cells were re-plated at low density in the presence of either hygromycin selection (125 μg/ml) for HP10 infected cells, or combined hygromycin (125 μg/ml) and G418 selection (500 μg/ml) for HP10E infected cells. A number of colonies were picked, expanded and assayed for the presence of episomal pHSV-HPRT by plasmid rescue. One clonal line from the HP10 infection and two clonal lines from the HP10E infection studied in detail were found to contain the intact episomal form of pHSV-HPRT (FIG. 4A). HUMHPRTB is a highly polymorphic tetranucleotide repeat marker found in intron 3 of the HPRT locus. Polymerase chain reaction (PCR)-based genotyping of HUMHPRTB was used to confirm the presence of the HPRT allele from pHSV-HPRT in the three transduced clonal lines (FIG. 4B). The copy number of pHSV-HPRT in the three lines was determined by quantitative Southern blotting to be approximately 1 copy/cell (FIG. 4C). Finally, strong HPRT activity was found in each of these three clonal lines after approximately two months of cell culture (FIG. 4D).

In Vivo HPRT Expression from pHSV-HPRT

Gene expression from pHSV-HPRT in vivo is being studied in the brains of the hprt-/- mouse strain B6.129P2-Hprt$^{b-m3}$. Ten microliters of pHSV-HPRT amplicon at 10$^6$ tu/ml will be injected into one hemisphere of a mouse brain, with 10 μl of saline solution injected into the other hemisphere as a negative control. Expression of the reporter gene GFP will be determined by direct detection of fluorescence and by antibody staining. HPRT expression will be assayed in brain slices using a [$^3$H]-hypoxanthine incorporation assay.

Expression of Human Low Density Lipoprotein Receptor from a 135 kb Genomic DNA BAC Insert Delivered by Infection A library BAC clone containing the complete 45 kb locus of the human low density lipoprotein receptor (LDLR)

contained within a 135 kb genomic DNA insert was identified (clone 164O19). The clone was retrofitted as described above with two HSV-1 amplicon vectors. First, vector pHG was used to convert the LDLR BAC into a HSV-1 amplicon (FIG. 5A). Second, the vector pEHHG (described above) was used to convert the LDLR BAC into a HSV-1/EBV hybrid amplicon (FIG. 5D). Both amplicons were prepared as described and used to infect MRC-5V2 cells at an MOI of ~1 (FIG. 5B and FIG. 5E). The infections were ~50–75% efficient, as judged by GFP reporter gene expression. Plasmid rescue on the infected MRC-5V2 cells revealed the pHSV-LDLR and pHSV/EBV-LDLR amplicons to be rescued intact with 75% and 57% efficiency, respectively.

The pHSV-LDLR amplicon was used to infect CHO ldlr-/- a7 cells expressing the Herpes virus entry protein C (HveC). Seventy-two hours postinfection, vector delivery was measured by GFP expression (FIG. 6B) and delivery of a functional LDLR was assayed using uptake of DiI-LDL, a fluorescently labelled form of LDL (FIG. 6C). The strong DiI fluorescence indicates expression from the genomic LDLR locus carried by pHSV-LDLR.

DISCUSSION

The vector system described has a number of advantages. It combines the ease of manipulation of the BAC and PAC cloning systems, the efficiency and large transgene capacity of HSV-1 amplicon gene delivery, and the extrachromosomal maintenance mechanism of EBV-based episomes. As such, it represents a potentially powerful new technology for functional genomics and gene therapy. HSV-1 amplicons are an excellent platform for the delivery of BAC and PAC inserts because: (i) HSV-1 has a high transgene capacity of approximately 150 kb; (ii) high-titre amplicon stocks can be produced by helper virus-free packaging systems; and (iii) the resulting virion particles have a broad cell tropism across a wide range of species. We believe HSV-1 is unique in being able to combine all these features. Other large insert systems (such as EBV or CMV) are not able to combine all of the features that HSV-1 can.

In this Example, a simple method for converting any BAC or PAC library clone into an HSV-1 amplicon is presented. Moreover, this Example demonstrates for the first time that HSV-1 amplicon vectors can deliver BAC and PAC genomic DNA inserts of over 100 kb. The amplicons were packaged into virions by our HSV-1 helper virus-free packaging system (Saeki, Y., et al., *Molecular Therapy* (2001), supra; International Patent Publication WO 00/34497 and were able to recircularize following infection. The vector also incorporates the episomal retention elements from EBV leading to prolonged extra-chromosomal maintainance. Although the Cre/loxP system was utilized here to convert PACs and BACs into HSV-1/EBV hybrid amplicons, the technique could be used to add any vector features to a BAC/PAC library clone. All BAC/PAC library vectors contain a single loxP site, which gives the technique broad applicability. Sequenced clones available from established libraries can be used.

In this Example, the HSV-1/EBV hybrid vector was able to package and deliver inserts of >100 kb intact with efficiencies between 25%-100%. Most BAC/PAC clones within current libraries fall within this size range. To demonstrate that genomic loci transferred in this way are functional, two complete genomic loci were delivered and assayed for expression. First, the 44 kb HPRT locus was delivered within a 115 kb BAC insert to a human HPRT-deficient fibroblast cell line. The infectious HPRT genomic DNA transgene was active both in a transient infection assay, and in selected clonal cell lines grown for prolonged periods of time following infection. Furthermore, it is expected that the insert will be functional in vivo following injection into the brains of hprt-deficient mice. Second, the 45 kb locus of the LDLR locus contained within a 135 kb genomic DNA BAC insert was delivered to the CHO ldlr-/- a7 cell line. Uptake assays using a fluorescently labelled form of LDL showed the gene was strongly expressed.

The infectious delivery of large genomic inserts has a number of applications. Functional analysis of BAC and PAC clones may prove useful in gene identification projects, especially in the final phase of identifying functional genes from a physically mapped region. The near-complete coverage of the human genome by BAC contigs, many of which are also completely sequenced, renders BACs the ideal starting point in functional genomics studies. The size range of intact amplicon delivery demonstrated here (~100–150 kb) makes the system ideally suited to the manipulation of BAC and PAC clones isolated from current libraries.

One challenge for post-sequence genomics is the elucidation of regulatory mechanisms of gene expression. Such studies require methods for routine manipulation of genomic DNA, and the means of efficient delivery to model systems, either in cell culture or in vivo. The vector described in this Example is a shuttle vector which can first be manipulated in bacteria and then transferred to a variety of mammalian cell types by infection where expression can be assayed. The ability to shuttle the vector back into bacteria means that the intactness of the construct can be easily confirmed.

Another challenge in genomics research lies in identifying polymorphisms in genes which lead to susceptibility to common, complex "polygenic" diseases (Altshuler, D., et al., *Nature Genet.* 26:135–137 (2000)). The vector system described potentially offers a simple method to test the functional significance of the large number of gene-associated single-nucleotide polymorphisms, including those recently found in non-coding regions (Horikawa, Y., et al., *Nature Genet.* 26:163–175 (2000)). Site-specific recombination in bacteria can be used to introduce a mutation in a BAC clone (Yang, X. W., et al., *Nature Biotechnol.* 15:859–865 (1997); Nefedov, M., et al., *Nucleic Acids Res.* 28:e79 i–iv (2000); Zhang, Y., et al., *Nature Genet.* 20:123–128 (1998)) which can then be transferred into an appropriate cell culture model. Finally, the ability to transfer large genomic DNA inserts by infectious delivery allows genomic DNA transgenes to be used in gene therapy approaches. By using a complete genomic locus as a therapeutic transgene, endogenous controlling elements can be included which may prove critical to ensure prolonged, regulated and tissue-specific transgene expression.

Example 2

A Rapid Method for the Production of Oncolytic HSV-1 Vectors

Herpes simplex virus type-1 (HSV-1) mutants lacking the UL39 (encoding ribonucleotide reductase, ICP6) and both copies of the γ34.5 gene (e.g., MGH1, G207) show oncolytic effects as well as potent immunizing effects. Furthermore, they are quite attenuated compared to the wild-type virus and proven to be safe through a number of in vivo safety studies. Such mutants thus provide optimal templates to produce novel replication-conditional HSV-1 vectors for cancer gene therapy applications. However, engineering a new HSV-1 mutant using conventional methods (based on homologous recombination in mammalian cells) is laborious and time-consuming. Thus, development of improved methods for generating these mutants facilitates the identification of optimal therapeutic genes and vector design.

In this Example, the inventors report on a quick, simple, and efficient system for the generation of oncolytic HSV-1 vectors (designated as the "HSVQuik system"). See, FIG. 7. This system consists of two components: a bacterial artificial chromosome (BAC) clone containing the backbone HSV-1 sequence (fHSVQuik-1, ~160 kb); and a transgene-transfer plasmid (pTransfer, 2 kb). HSVQuik takes advantages of the two different site-specific recombination systems, Cre-loxP and Flp-FRT. The fHSVQuik-1 contains a circular form of the HSV-1 genome with deletions in the UL39 gene and both copies of the γ34.5 gene (derived from the MGH-1). The BAC backbone of the plasmid is inserted at the deleted UL39 locus, flanked by a loxP site and a FRT site, and contains a copy of the red fluorescent protein (RFP) gene as an indicator of the BAC backbone. The BAC backbone also carries the chloramphenicol-resistance gene ($Cm^r$). In addition, the EGFP gene was inserted in frame downstream from the remaining UL39 coding sequence, so that it expresses an ICP6 (ΔC)-EGFP fusion protein under control of the ICP6 promoter. The plasmid, pTransfer, is a replication-conditional plasmid (R6Kγ-based) and contains a multiple cloning site (MCS) flanked by a loxP site and a FRT site.

First, a series of transfer plasmids were constructed containing one or more transgene cassettes of interest. A transgene cassette of interest (X) was cloned into the MCS of pTransfer. Then, the entire transfer plasmid was inserted into the UL39 locus of the fHSVQuik-1 through Flp-mediated site-specific recombination in *E. coli*. The efficiency of obtaining correct co-integrates is high (up to 80% of the obtained clones possess the expected restriction enzyme-HindIII-pattern; see, FIG. 9) and the procedure is rapid. The resulting HSV-1 precursor BAC clones can be stored as bacterial stocks for further modifications and the BAC DNA can easily be purified by conventional alkaline methods. When the HSV-1 precursor DNA and a Cre recombinase-expressing plasmid were cotransfected into VERO cells, the prokaryotic backbone of the precursor was excised out through recombination of the two loxP sites and the viral genome containing the transgenes of interest was released. Indeed, after a single round of limited dilution of progeny viruses, a number of clones with GFP but without RFP were obtained. The loss of RFP expression can be used as an indicator for successful removal of BAC backbone. See, FIG. 10. Further analyses by PCR confirmed the correct genetic identities of the progeny viruses. See, FIG. 11. Characterization of rHsvQ1 by a one-step growth curve, in vivo safety study on BALB/c mice, and cytopathic effect in vitro, are presented in FIG. 12. HSVQuik will allow the rapid and high throughput generation of complex oncolytic viruses for cancer therapy, or other uses, in approximately 2–3 weeks.

Example 3

A Rapid Method for the Production of Adenoviral Vectors

Adenoviral (Ad) vectors have been widely and successfully used to introduce foreign genes into a variety of mammalian cells both in vitro and in vivo. Ad vectors have the following advantages over other viral vectors: (1) they can be generated at very high titers; (2) highly purified vector stocks can easily be produced; (3) they can efficiently transduce not only dividing cells, but also non-dividing cells; and (4) the targeting of Ad vectors is possible by genetic modification of viral fiber proteins. Generation of a new Ad vector could be laborious and time-consuming. Thus, development of improved methods could have a significant impact on a variety of research fields. Currently available systems to generate Ad vectors utilize homologous recombination, Cre-mediated site-specific recombination, or direct ligation.

In this Example, the inventors report on a quick, simple, and efficient system to generate Ad vectors (designated as the "AdQuik system"). See, FIG. 8. This system consists of two components: an adenoviral backbone plasmid (pAdQuik-1, 37 kb); and a transgene-transfer plasmid (pTransfer-GC, 4.8 kb), and takes advantage of two different site-specific recombination systems (Cre-loxP and Flp-FRT). The pAdQuik-1 contains a circular form of the adenoviral genome with deletions in the E1 and E3 regions (derived from pALC-2 kindly provided by Drs. Tashiro and Miyazaki, Osaka Univ.). The pAdQuik-1 has a prokaryotic backbone, carrying the origin of DNA replication from plasmid p15A, the chloramphenicol-resistance gene (($Cm^r$), and two copies of the RFP gene as an indicator of plasmid backbone, inserted into the deleted E1 region of the Adenoviral genome. The pTransfer-GC is a replication-conditional plasmid and contains the EGFP gene as an indicator and a transgene cassette driven by the CMV promoter. The backbones of both plasmids were designed to be flanked by a loxP site on one side and a FRT site on the other.

First, a transfer plasmid was constructed by inserting a gene of interest (and potentially an additional transgene cassette) into the MCS of pTransfer-GC (3–4 days). Then, the entire transfer plasmid was inserted into the E1 region of the pAdQuik-1 at the FRT site by Flp-mediated site-specific recombination in *E. coli*. The efficiency of obtaining correct co-integrates is high (90–100 % of the obtained clones possess the expected restriction enzyme (XbaI) pattern; see, FIG. 13) and the procedure is rapid (3 days). The resulting Ad precursor plasmid can be stored either as a DNA preparation or as a bacterial stock and its DNA can easily be purified by conventional alkaline methods. When the Ad precursor DNA ([42+"size of the transgene"] kb) alone was transfected into 293 cells, no viral progenies were obtained because its size is beyond the Ad packaging capacity. However, when the Ad precursor DNA was cotransfected with a Cre recombinase-expressing plasmid, GFP-positive Ad plaques were readily obtained within 5 days after transfection. The generated progeny viruses were all GFP-positive, but RFP-negative. The loss of RFP expression can be used as an indicator for successful removal of BAC backbone. See, FIG. 14. PCR analyses of vector DNA confirmed its correct genetic structure (see, FIG. 15). AdQuik thus allows for the rapid and high throughput generation of Ad vectors, in approximately 2–3 weeks.

Example 4

Construction and Use of a Large Insert HSV-BAC Amplicon Library

INTRODUCTION

In this Example, the first infectious expression-ready genomic DNA library for use in functional genomics is constructed. A hybrid vector is used, combining the features of the bacterial artificial chromosome (BAC) cloning system in *E. coli*, with the herpes simplex virus type 1 (HSV-1)-based amplicon system for gene delivery to mammalian cells (Sena-Esteves et al., *Mol. Ther.* 2:9–15 (2000)). The BAC cloning system in *E. coli* has proved to be an excellent method for manipulating large genomic DNA inserts of up to 300 kb in size (Kim et al., *Genomics* 34:213–218 (1996); Osoegawa et al., *Genome Res.* 10:116–128 (2000)). We have shown that HSV-1 amplicons are an extremely efficient method of introducing and expressing genes within large genomic DNA inserts in a range of cell types (Wade-Martins et al., *Nature Biotechnol.* 19:1067–1070 (2001); see also Example 1). The large-insert amplicons have been shown to infect primary cells much more efficiently than these cells can be transfected.

A genomic DNA library is constructed and propagated within *E. coli* as a BAC, and then packaged and delivered to mammalian cells as an HSV-1 amplicon for studies on expression and function of genomic DNA.

RESULTS

Library Construction and Characterization

To create the library, the inserts and the vector are prepared as follows. Human genomic DNA is isolated from freshly prepared blood lymphocytes and embedded in agarose blocks. The DNA is partially digested with BamHI restriction enzyme, and digest fragments of size ~120–145 kb are isolated by gel purification using pulsed field gel electrophoresis. Partial digestion by other restriction enzymes (e.g.: EcoRI or HindIII) could also be used, as could shearing of genomic DNA to the correct size. In this Example, Bam HI partial digestion is preferred.

The library vector to be used is a hybrid vector in which HSV-1 derived elements (specifically, the $ori_s$ origin of replication, and the pac cleavage/packaging signal) have been added to a BAC vector. The resulting HSV-1 amplicon/BAC hybrid vector is named pHSV-BAC. This pHSV-BAC vector is digested with Bam HI, treated twice with calf intestinal phosphate to prevent self-ligation, and gel purified. Careful preparation of the vector to prevent self-ligation will result in ≦5% of clones containing no insert ("empty" clones) in the final library. The genomic DNA inserts are ligated into the BamHI site of the pHSV-BAC vector, and the ligation products are electroporated into high efficiency *E. coli* cells. Approximately 200,000 to 500,000 individual bacterial colonies are picked into Luria broth (plus chloramphenicol) cultures in 384-well plates and grown overnight. Glycerol stocks are prepared to make a master library and several copies. The library stocks are then stored at –80° C.

To characterize the new library, a representative sample of library clones are tested for: (i) the presence of "empty" clones consisting of self-ligated vector; (ii) the average insert size; and, (iii) insert stability over prolonged serial culture of bacterial clones. It is expected that the incidence of "empty" clones will be only ≦5%, that the average insert size will be approximately 135 kb, and that the library clones will be stable after prolonged serial culture in *E. coli*. The method is outlined in FIG. 16.

In this specific example, human genomic DNA is used for the source of inserts. Additional libraries are made in exactly the same way using other species genomic DNA as the source for inserts. Specifically, mouse and rat genomic DNA can be used as the source for inserts in the libraries.

Screening the Library and Obtaining Clones for Functional Studies

Two library screening platforms are created which allow the library to be screened based on DNA sequence at the individual clone level. First, high-density filters are prepared from the library stock cultures. The prepared filters are suitable for screening with DNA hybridization probes. Second, DNA samples are prepared from each clone, and pooled DNA stock plates are created such that the library can be entirely screened using the polymerase chain reaction (PCR) method. Positive clones are identified by a unique address, consisting of a plate number, followed by a row and column coordinate.

Once a clone is identified, it is then packaged as an HSV-1 amplicon and delivered to cells as follows. First, individual pHSV-BAC clones are prepared from *E. coli* cultures by routine methods and purified by double cesium chloride banding. Second, the pHSV-BAC clones are packaged using an improved helper virus-free system for HSV-1 amplicons (Saeki et al., *Mol. Ther.* 3:591–601 (2001)). The amplicon stock is concentrated by ultra-centrifugation and assayed for amplicon titer. Third, the library pHSV-BAC amplicons are used to infect appropriate model cell cultures, and gene expression from the amplicon is assayed. FIG. 17 shows functional expression from the pHSV-HPRT amplicon containing the genomic locus of the human hypoxanthine phosphoribosyltransferase (HPRT) gene delivered by infection to a human fibroblast cell line otherwise lacking HPRT activity (Wade-Martins et al., *Nature Biotechnol.* 19:1067–1070 (2001)). The library screening method is outlined in FIG. 17.

Library Screening by Functional Assay

The basis of the library screening method described above is by comparison with a known sequence, using either a DNA hybridization probe, or a pair of PCR primers. An alternative screening methodology, outlined in FIG. 18 and described below, is by functional screening.

An assay is previously arranged in which a certain function can be tested within a specific cell culture model. The entire pHSV-BAC library is packaged by the improved helper virus-free system, either as one mixed library, or using a clone-by-clone approach. The cell culture model is arranged in a high-density cell array. The array is established in either a multi-well (e.g., 384 well) format, or in a high-density array of cell clusters (Ziauddin and Sabatini, *Nature* 411:107–110 (2001)). The cell array is infected by the pHSV-BAC library after which a functional assay is performed on infected cells.

Those cells which show a positive result for the predetermined function being tested are analyzed further. The PHSV-BAC vector is rescued from the infected cells, shuttled back to *E. coli*, and the ends are sequenced to determine the location of the pHSV-BAC clone within the human genome sequence (The International Human Genome Sequencing Consortium, *Nature* 409:860–921 (2001)). Further functional analyses of the genes located within the pHSV-BAC clone are then performed. This combination strategy of functional screening, and reference back to the fully sequenced human genome, provides a rapid method of assigning novel function to genes.

CONCLUSION

This novel library is the first infectious, expression-ready, genomic DNA library. It combines the known advantages of the BAC cloning system with the recently discovered ability of HSV-1-based amplicons to deliver and express large genomic DNA inserts in a range of cell types.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A method for converting a large capacity cloning vector into a herpes simplex virus (HSV)-based amplicon, said method comprising recombining:
    (a) a large capacity cloning vector comprising a genomic DNA insert; and
    (b) an amplicon vector comprising a herpesvirus cleavage/packaging sequence and a herpesvirus origin of replication;
    thereby producing an HSV-based amplicon vector comprising said genomic DNA insert; wherein said large capacity cloning vector is a bacterial artificial chromosome (BAC), P1 phage-based vector (PAC), cosmid, yeast artificial chromosome (YAC), or viral based vector.

2. The method of claim 1, wherein said herpesvirus cleavage/packaging sequence is an HSV-1 cleavage/packaging sequence.

3. The method of claim 1, wherein said herpesvirus origin of replication is an HSV-1 origin of replication.

4. The method of claim 1, wherein said herpesvirus cleavage/packaging sequence is an HSV-1 cleavage/packaging sequence, and said herpesvirus origin of replication is an HSV-1 origin of replication.

5. The method of claim 1, wherein said amplicon vector of (b) further comprises a genetic element from Epstein-Barr virus (EBV).

6. The method of claim 5, wherein said genetic element from EBV is oriP.

7. The method of claim 1, wherein said large capacity cloning vector is a bacterial artificial chromosome (BAC).

8. The method of claim 1, wherein said large capacity cloning vector is a P1 phage-based vector (PAC).

9. The method of claim 1, wherein said recombining comprises site-specific recombination of (a) and (b) in the presence of a site-specific recombinase.

10. The method of claim 9, wherein said site-specific recombinase is selected from the group consisting of: P1 bacteriophage CRE, yeast FLP, and yeast R recombinase.

11. The method of claim 9, wherein said site-specific recombinase is P1 bacteriophage CRE.

12. The method of claim 1, wherein said recombining comprises homologous recombination of (a) and (b).

13. The method of claim 1, wherein said recombining comprises ligation of (a) and (b).

14. The method of claim 1, wherein said genomic DNA insert is 50 to 100 kb in size.

15. The method of claim 1, wherein said genomic DNA insert is 110 to 150 kb in size.

16. The method of claim 1, further comprising packaging said HSV-based amplicon vector comprising said genomic DNA insert into an infectious particle.

17. The method of claim 16, wherein said packaging is accomplished using a helper virus-free system.

* * * * *